(12) United States Patent
Bailey et al.

(10) Patent No.: US 6,908,901 B2
(45) Date of Patent: Jun. 21, 2005

(54) HEPATITIS C INHIBITOR PEPTIDE ANALOGS

(75) Inventors: Murray D. Bailey, Pierrefonds (CA); Montse Llinas-Brunet, Dollard-des-Ormeaux (CA)

(73) Assignee: Boehringer Ingelheim International, GmbH, Ingelheim (DE)

( * ) Notice: Subject to any disclaimer, the term of this patent is extended or adjusted under 35 U.S.C. 154(b) by 0 days.

(21) Appl. No.: 10/791,318

(22) Filed: Mar. 2, 2004

(65) Prior Publication Data

US 2004/0224900 A1 Nov. 11, 2004

Related U.S. Application Data

(60) Provisional application No. 60/452,187, filed on Mar. 5, 2003.

(51) Int. Cl.$^7$ .......................... A61K 38/16; A61K 38/00
(52) U.S. Cl. .............................................. 514/18; 514/2
(58) Field of Search ........................................ 514/2, 18

(56) References Cited

U.S. PATENT DOCUMENTS

| | | | | |
|---|---|---|---|---|
| 6,323,180 B1 | * | 11/2001 | Llinas-Brunet et al. | ........ 514/18 |
| 6,329,379 B1 | * | 12/2001 | Llinas-Brunet et al. | ..... 514/256 |
| 6,410,531 B1 | * | 6/2002 | Llinas-Brunet et al. | .. 514/235.5 |
| 6,420,380 B2 | * | 7/2002 | Llinas-Brunet et al. | ..... 514/289 |
| 6,534,523 B1 | | 3/2003 | Llinas-Brunet et al. | |
| 6,642,204 B2 | * | 11/2003 | Llinas-Brunet et al. | ........ 514/18 |

FOREIGN PATENT DOCUMENTS

| WO | WO 99/07733 A2 | 2/1999 |
|---|---|---|
| WO | WO 00/09543 A2 | 2/2000 |
| WO | WO 00/09558 A1 | 2/2000 |

OTHER PUBLICATIONS

Naps and Johns; Optically active mono–substituted sucolnic acids and derivatives; Journal of American Chemical Society, vol. 62, 1940, pp. 2450–2457.

* cited by examiner

*Primary Examiner*—Christopher Tate
*Assistant Examiner*—Thomas S. Heard
(74) *Attorney, Agent, or Firm*—Michael P. Morris; Phillip I. Datlow

(57) ABSTRACT

Compounds of formula (I):

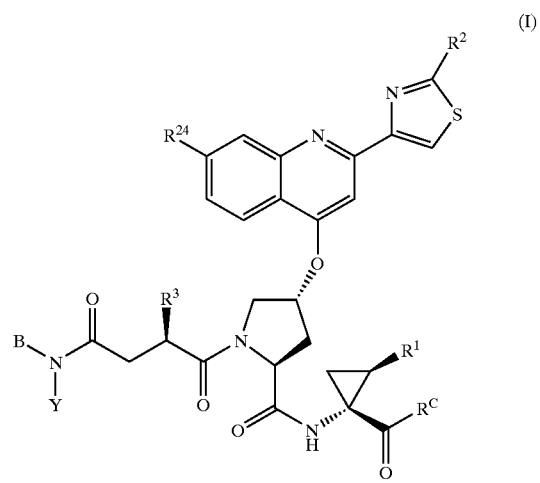

wherein B, Y, $R^3$, $R^{24}$, $R^2$, $R^1$ and $R^C$ are defined herein. The compounds are useful as inhibitors of HCV NS3 protease.

40 Claims, No Drawings

SEQUENCE LISTING

<160> NUMBER OF SEQ ID NOS: 3

<210> SEQ ID NO 1
<211> LENGTH: 30
<212> TYPE: DNA
<213> ORGANISM: Artificial
<220> FEATURE:
<223> OTHER INFORMATION: Forward primer

<400> SEQUENCE: 1
acgcagaaag cgtctagcca tggcgttagt                    30

<210> SEQ ID NO 2
<211> LENGTH: 30
<212> TYPE: DNA
<213> ORGANISM: Artificial
<220> FEATURE:
<223> OTHER INFORMATION: Reverse primer

```
<400> SEQUENCE: 2
tcccggggca ctcgcaagca ccctatcagg                              30

<210> SEQ ID NO 3
<211> LENGTH: 26
<212> TYPE: DNA
<213> ORGANISM: Artificial
<220> FEATURE:
<223> OTHER INFORMATION: PUTR probe

<400> SEQUENCE: 3
tggtctgcgg aaccggtgag tacacc                                  26
```

HEPATITIS C INHIBITOR PEPTIDE ANALOGS

This application claims benefit from U.S. Provisional Application No. 60/452,187, filed Mar. 5, 2003, which application is herein incorporated by reference.

FIELD OF THE INVENTION

The present invention relates to compounds, processes for their synthesis, compositions and methods for the treatment of hepatitis C virus (HCV) infection. In particular, the present invention provides novel peptide analogs, pharmaceutical compositions containing such analogs and methods for using these analogs in the treatment of HCV infection.

BACKGROUND OF THE INVENTION

Hepatitis C virus (HCV) is the major etiological agent of post-transfusion and community-acquired non-A non-B hepatitis worldwide. It is estimated that over 200 million people worldwide are infected by the virus. A high percentage of carriers become chronically infected and many progress to chronic liver disease, so-called chronic hepatitis C. This group is in turn at high risk for serious liver disease such as liver cirrhosis, hepatocellular carcinoma and terminal liver disease leading to death.

The mechanism by which HCV establishes viral persistence and causes a high rate of chronic liver disease has not been thoroughly elucidated. It is not known how HCV interacts with and evades the host immune system. In addition, the roles of cellular and humoral immune responses in protection against HCV infection and disease have yet to be established. Immunoglobulins have been reported for prophylaxis of transfusion-associated viral hepatitis, however, the Center for Disease Control does not presently recommend immunoglobulins treatment for this purpose. The lack of an effective protective immune response is hampering the development of a vaccine or adequate post-exposure prophylaxis measures, so in the near-term, hopes are firmly pinned on antiviral interventions.

Various clinical studies have been conducted with the goal of identifying pharmaceutical agents capable of effectively treating HCV infection in patients afflicted with chronic hepatitis C. These studies have involved the use of interferon-alpha, alone and in combination with other antiviral agents. Such studies have shown that a substantial number of the participants do not respond to these therapies, and of those that do respond favorably, a large proportion were found to relapse after termination of treatment.

Until recently, interferon (IFN) was the only available therapy of proven benefit approved in the clinic for patients with chronic hepatitis C. However the sustained response rate is low, and interferon treatment also induces severe side-effects (i.e. retinopathy, thyroiditis, acute pancreatitis, depression) that diminish the quality of life of treated patients. Recently, interferon in combination with ribavirin has been approved for patients non-responsive to IFN alone. However, the side effects caused by IFN are not alleviated with this combination therapy. Pegylated forms of interferons such as PEG-Intron® and Pegasys®) can apparently partially address these deleterious side-effects but antiviral drugs still remain the avenue of choice for oral treatment of HCV.

Therefore, a need exists for the development of effective antiviral agents for treatment of HCV infection that overcome the limitations of existing pharmaceutical therapies.

HCV is an enveloped positive strand RNA virus in the Flaviviridae family. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature nonstructural proteins (NS2, NS3, NS4A, NS4B, NS5A, and NS5B) is effected by two viral proteases. The first one, as yet poorly characterized, cleaves at the NS2—NS3 junction (henceforth referred to as NS2/3 protease); the second one is a serine protease contained within the N-terminal region of NS3 (NS3 protease) and mediates all the subsequent cleavages downstream of NS3, both in cis, at the NS3—NS4A cleavage site, and in trans, for the remaining NS4A-NS4B, NS4B-NS5A, NS5A-NS5B sites. The NS4A protein appears to serve multiple functions, acting as a cofactor for the NS3 protease and possibly assisting in the membrane localization of NS3 and other viral replicase components. The complex formation of the NS3 protease with NS4A seems necessary to the processing events, enhancing the proteolytic efficiency at all of the sites. The NS3 protein also exhibits nucleoside triphosphatase and RNA helicase activities. NS5B is a RNA-dependent RNA polymerase that is involved in the replication of HCV.

A general strategy for the development of antiviral agents is to inactivate virally encoded enzymes that are essential for the replication of the virus.

In WO 00/09543, compounds of the formula

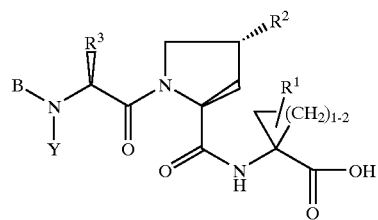

wherein a preferred meaning of $R^2$ is an unsubstituted or mono- or disubstituted quinolinyl residue as defined therein, are described as hepatitis C viral NS3 protease inhibitors, an enzyme essential for the replication of the hepatitis C virus.

The present invention now provides structurally different less peptidic compounds that are inhibitory to the NS3 protease. Furthermore, compounds being active in cell culture are provided.

An advantage of one aspect of the present invention resides in the fact that compounds according to this invention specifically inhibit the NS3 protease and do not show significant inhibitory activity against other serine proteases such as human leukocyte elastase (HLE), porcine pancreatic elastase (PPE), or bovine pancreatic chymotrypsin, or cysteine proteases such as human liver cathepsin B (Cat B).

SUMMARY OF THE INVENTION

Included in the scope of the invention is a racemate, diastereoisomer, or optical isomer of a compound of formula (I):

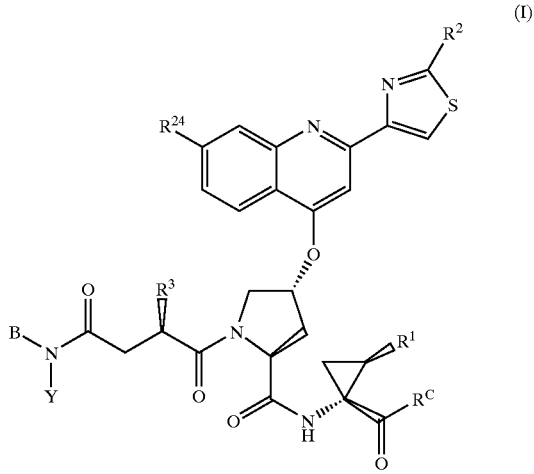

wherein:
- B is $(C_{2-10})$alkyl, $(C_{3-7})$cycloalkyl or $(C_{1-4})$alkyl-$(C_{3-7})$cycloalkyl,
  a) wherein said cycloalkyl and alkyl-cycloalkyl may be mono-, di- or tri-substituted with $(C_{1-3})$alkyl; and
  b) wherein said alkyl, cycloalkyl and alkyl-cycloalkyl may be mono- or di-substituted with substituents selected from hydroxy and O—$(C_{1-4})$alkyl; and
  c) wherein each of said alkyl-groups may be mono-, di- or tri-substituted with halogen; and
  d) wherein in each of said cycloalkyl groups being 5-, 6- or 7-membered, one or two —CH$_2$-groups not being directly linked to each other may be replaced by —O— such that the O-atom is linked to the N atom to which B is attached via at least two C-atoms; or B is phenyl, $(C_{1-3})$alkyl-phenyl, heteroaryl or $(C_{1-3})$alkyl-heteroaryl, wherein the heteroaryl-groups are 5- or 6-membered having from 1 to 3 heteroatoms selected from N, O and S; wherein said phenyl and heteroaryl groups may be mono-, di- or trisubstituted with substituents selected from halogen, —OH, $(C_{1-4})$alkyl, O—$(C_{1-4})$alkyl, S—$(C_{1-4})$alkyl, —NH$_2$, —NH(($C_{1-4}$)alkyl) and —N(($C_{1-4}$)alkyl)$_2$, —CONH$_2$ and —CONH—$(C_{1-4})$alkyl;

Y is H or $(C_{1-6})$alkyl;

$R^3$ is $(C_1)$alkyl, $(C_{3-7})$cycloalkyl or $(C_{1-3})$alkyl-$(C_{3-7})$cycloalkyl, wherein each of said cycloalkyl groups may be mono-, di- or tri-substituted with substituents selected from halogen, —OH, $(C_{1-4})$alkyl, O—$(C_{1-4})$alkyl, S—$(C_{1-4})$alkyl, —NH$_2$, —NH(($C_{1-4}$)alkyl), —N(($C_{1-4}$)alkyl)$_2$, —COOH and —CONH$_2$;

$R^2$ is $R^{20}$, —NR$^{21}$R$^{22}$, —NR$^{22}$COR$^{20}$, —NR$^{22}$COOR$^{20}$ or —NR$^{22}$CONR$^{23}$R$^{21}$, wherein
  $R^{20}$ is selected from $(C_1)$alkyl, $(C_{3-7})$cycloalkyl and $(C_{1-4})$alkyl-$(C_{3-7})$cycloalkyl, wherein said alkyl, cycloalkyl and alkyl-cycloalkyl may be mono-, di- or tri-substituted with $(C_{1-3})$alkyl; and
  $R^{21}$ is H or $R^{20}$ as defined above,
  $R^{22}$ and $R^{23}$ are independently selected from H and methyl, and
  $R^{24}$ is selected from: —O—$(C_{1-4})$alkyl, NH(($C_{1-4}$)alkyl) and —N(($C_{1-4}$)alkyl)$_2$;

$R^1$ is $(C_1)$alkyl or $(C_{2-6})$alkenyl; and $Rc^C$ is hydroxy or NHSO$_2$R$^5$ wherein $R^5$ is $(C_1)$alkyl, $(C_{3-7})$cycloalkyl, $(C_1)$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; all of which being optionally mono-, di- or tri-substituted with substituents selected from halogen, hydroxy, cyano, $(C_{1-4})$alkyl, O—$(C_{1-6})$alkyl, —CO—NH$_2$, —CO—NH(($C_{1-4}$)alkyl), —CO—N(($C_{1-4}$)alkyl)$_2$, —NH$_2$, —NH(($C_{1-4}$)alkyl) and —N(($C_{1-4}$)alkyl)$_2$; wherein $(C_{1-4})$alkyl and O—$(C_{1-6})$alkyl are optionally mono-, di- or trisubstituted with halogen; and all of which optionally being monosubstituted with nitro;

or a pharmaceutically acceptable salt or ester thereof.

Included within the scope of this invention is a pharmaceutical composition comprising an anti-hepatitis C virally effective amount of a compound of formula 1, or a pharmaceutically acceptable salt or ester thereof, in admixture with a pharmaceutically acceptable carrier medium or auxiliary agent.

According to a further aspect of this embodiment the pharmaceutical composition according to this invention comprises a therapeutically effective amount of at least one other antiviral agent.

Another important aspect of the invention involves a method of treating or preventing a hepatitis C viral infection in a mammal by administering to the mammal an anti-hepatitis C virally effective amount of a compound of formula I, a pharmaceutically acceptable salt or ester thereof, or a composition as described above, alone or in combination with at least one other antiviral agent, administered together or separately.

Also within the scope of this invention is the use of a compound of formula I as described herein, or a pharmaceutically acceptable salt or ester thereof, for the manufacture of a medicament for the treatment or prevention of hepatitis C viral infection.

Still another aspect of this invention relates to a method of inhibiting the replication of hepatitis C virus by exposing the virus to a hepatitis C viral NS3 protease inhibiting amount of the compound of formula (I) according to this invention, or a pharmaceutically acceptable salt or ester thereof.

A further aspect of this invention relates to a process for the preparation of a peptide analog of formula (I) as described hereinbefore comprising the step of coupling a peptide of the formula (III):

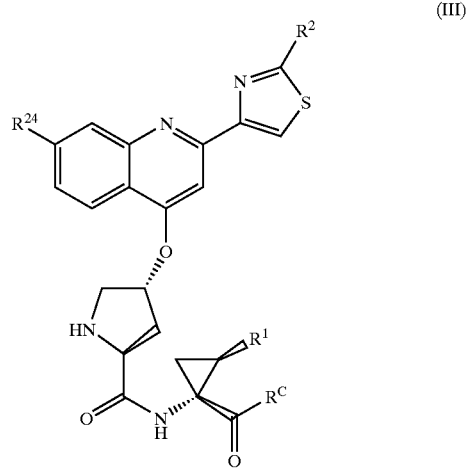

wherein $R^C$ is —O—CGP or —NHSO$_2$R$^S$; and $R^1$, $R^2$, $R^{24}$ and $R^S$ are as defined hereinbefore and CPG is a carboxylprotecting group;

with a succinic acid moiety of formula (II):

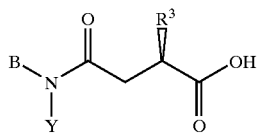

(II)

wherein B, Y and R³ are as defined hereinbefore.

Another aspect of this invention is related to the succinic acid derivative of the formula (II)

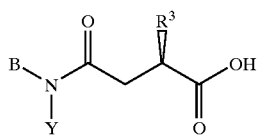

(II)

wherein B, Y and R³ are as defined hereinbefore.

A further aspect of the invention is the use of a succinic acid derivative of the formula (II) as described hereinbefore for the preparation of:

a) a serine protease inhibitor peptide analog; or b) a HCV NS3 protease inhibitor peptide analog.

An additional aspect of this invention refers to an article of manufacture comprising packaging material contained within which is a composition effective to treat an HCV infection or to inhibit the NS3 protease of HCV and the packaging material comprises a label which indicates that the composition can be used to treat infection by the hepatitis C virus, and wherein said composition comprises a compound of formula (I) according to this invention or a pharmaceutically acceptable salt or ester thereof.

DETAILED DESCRIPTION OF PREFERRED EMBODIMENTS

Definitions

As used herein, the following definitions apply unless otherwise noted: With reference to the instances where (R) or (S) is used to designate the absolute configuration of a substituent or asymmetric center of a compound of formula I, the designation is done in the context of the whole compound and not in the context of the substituent or asymmetric center alone.

The designation "P1, P2, and P3" as used herein refer to the position of the amino acid residues starting from the C-terminus end of the peptide analogs and extending towards the N-terminus (i.e. P1 refers to position 1 from the C-terminus, P2: second position from the C-terminus, etc.) (see Berger A. & Schechter I., Transactions of the Royal Society London series B257, 249–264 (1970)).

As used herein the term "(1R, 2S)-vinyl-ACCA" refers to a compound of formula:

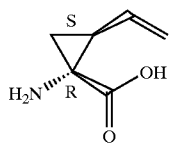

namely, (1R, 2S) 1-amino-2-ethenylcyclopropanecarboxylic acid.

The term "$(C_{1-n})$alkyl" as used herein, either alone or in combination with another substituent, means acyclic, straight or branched chain alkyl substituents containing from 1 to n carbon atoms. "$(C_{1-6})$alkyl" includes, for example, methyl, ethyl, n-propyl, n-butyl, 1-methylethyl (i-propyl), 1-methylpropyl, 2-methylpropyl, 1,1-dimethylethyl (tert-butyl), pentyl and hexyl. The acronym Me denotes a methyl group.

The term "$(C_{3-7})$cycloalkyl" as used herein, either alone or in combination with another substituent, means a cycloalkyl substituent containing from 3 to 7 carbon atoms and includes cyclopropyl, cyclobutyl, cyclopentyl, cyclohexyl and cycloheptyl.

The term "$(C_{3-7})$alkyl-$(C_{3-7})$cycloalkyl" as used herein means an alkylene radical containing 1 to n carbon atoms to which a cycloalkyl radical containing from 3 to 7 carbon atoms is directly linked; for example, cyclopropylmethyl, cyclopentylethyl, cyclohexylmethyl, cyclohexylethyl and cycloheptylpropyl.

The term "$C_6$ or $C_{10}$ aryl" as used herein, either alone or in combination with another radical, means either an aromatic monocyclic group containing 6 carbon atoms or an aromatic bicyclic group containing 10 carbon atoms. For example, aryl includes phenyl, 1-naphthyl or 2-naphthyl.

The term "heteroaryl" as used herein, either alone or in combination with another radical, means a five- or six-membered monocyclic heterocyclic aromatic group containing from one to three heteroatoms selected from oxygen, nitrogen and sulfur. Examples of heteroaryl include, but are not limited to, pyrrole, thiophene, 1H-imidazole, isoxazole, oxazole, thiazole, triazole, tetrazole, pyridine, piperazine or pyrimidine.

As used herein, the term "alkyl-aryl" means an alkyl radical to which an aryl is bonded. Examples of $(C_{1-3})$alkyl-aryl are benzyl (phenylmethyl), phenylethyl and phenylpropyl.

The term "O—$(C_{1-n})$alkyl" or "$(C_{1-n})$alkoxy" as used herein, either alone or in combination with another radical, means the radical —O—$(C_{1-n})$alkyl wherein alkyl is as defined above containing up to n carbon atoms, and includes methoxy, ethoxy, propoxy, 1-methylethoxy, butoxy and 1,1-dimethylethoxy. The latter radical is known commonly as tert-butoxy.

The term "halo" as used herein means a halogen substituent selected from fluoro, chloro, bromo or iodo.

The term "pharmaceutically acceptable ester" as used herein, either alone or in combination with another substituent, means esters of the compound of formula I in which any of the carboxyl functions of the molecule, but preferably the carboxy terminus, is replaced by an alkoxycarbonyl function:

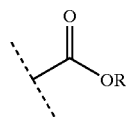

in which the R moiety of the ester is selected from alkyl (e.g. methyl, ethyl, n-propyl, t-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl); aryl (e.g. phenyl), optionally substituted with halogen, $C_{1-4}$ alkyl or $C_{1-4}$ alkoxy. Other suitable prodrug esters can be found in Design of prodrugs, Bundgaard, H. Ed. Elsevier (1985) incorporated herein by reference. Such pharmaceutically acceptable esters are usually hydrolyzed in vivo when injected in a mammal and transformed into the acid form of the compound of formula I.

With regard to the esters described above, unless otherwise specified, any alkyl moiety present preferably contains 1 to 16 carbon atoms, particularly 1 to 6 carbon atoms. Any aryl moiety present in such esters preferably comprises a phenyl group.

In particular the esters may be a $C_{1-16}$ alkyl ester, an unsubstituted benzyl ester or a benzyl ester substituted with at least one halogen, $C_{1-6}$ alkyl, $C_{1-6}$ alkoxy, nitro or trifluoromethyl.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1–19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethane-sulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "mammal" as it is used herein is meant to encompass humans, as well as non-human mammals which are susceptible to infection by hepatitis C virus including domestic animals, such as cows, pigs, horses, dogs and cats, and non-domestic animals.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Such agents can be selected from: another anti-HCV agent, HIV inhibitor, HAV inhibitor and HBV inhibitor. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as $\alpha$-, $\beta$-, $\delta$- and omega interferons, tau-interferons, consensus interferons and asialo-interferons), class 11 interferons (such as $\gamma$-interferons) and pegylated forms thereof.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929, WO 03/064416, WO 03/064455, WO 03/064456, WO 02/060926, WO 03/053349, WO 03/099316 or WO 03/099274, and the Vertex pre-development candidate identified as VX-950.

The term "inhibitor of HCV polymerase" as used herein means an agent (compound or biological) that is effective to inhibit the function of an HCV polymerase in a mammal. This includes, for example, inhibitors of HCV NS5B polymerase. Inhibitors of HCV polymerase include non-nucleosides, for example, those compounds described in:

U.S. application Ser. No. 60/441,674 filed Jan. 22, 2003, herein incorporated by reference in its entirety (Boehringer Ingelheim), U.S. application Ser. No. 60/441,871 filed Jan. 22, 2003, herein incorporated by reference in its entirety (Boehringer Ingelheim), U.S. application Ser. No. 10/198,680 filed 18 Jul. 2002, herein incorporated by reference in its entirety, which corresponds to WO 03/010140 (Boehringer Ingelheim), U.S. application Ser. No. 10/198,384 filed 18 Jul. 2002, herein incorporated by reference in its entirety, which corresponds to WO 03/010141 (Boehringer Ingelheim), U.S. application Ser. No. 10/198,259 filed 18 Jul. 2002, herein incorporated by reference in its entirety, which corresponds to WO 03/007945 (Boehringer Ingelheim), WO 03/026587 (Bristol Myers Squibb);
WO 02/100846 A1 and WO 02/100851 A2 (both Shire),
WO 01/85172 A1 and WO 02/098424 A1 (both GSK),
WO 00/06529 and WO 02/06246 A1 (both Merck),
WO 01/47883 and WO 03/000254 (both Japan Tobacco) and
EP 1 256 628 A2 (Agouron).

Furthermore other inhibitors of HCV polymerase also include nucleoside analogs, for example, those compounds described in:
WO 01/90121 A2 (Idenix);
WO 02/069903 A2 (Biocryst Pharmaceuticals Inc.), and
WO 02/057287 A2 and WO 02/057425 A2 (both Merck/Isis).

Specific examples of inhibitors of an HCV polymerase, include JTK-002/003 and JTK-109 (Japan Tobacco) and NM-283 (Idenix).

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal. Inhibitors of another target in the HCV life cycle include, for example, agents that inhibit a target selected from helicase, NS2/3 protease and internal ribosome entry site (IRES). Specific examples of inhibitors of another target in the HCV life cycle include ISIS-14803 (ISIS Pharmaceuticals).

The term "HIV inhibitor" as used herein means an agents (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleosidic inhibitors, non-nucleosidic inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include α-, β-, δ-, ω-interferons, τ-interferons, consensus interferons, asialo-interferons and pegylated forms thereof.

The term "class II interferon" as used herein means an interferon selected from a group of interferons that all bind to receptor type II. Examples of class II interferons include γ-interferons.

Specific preferred examples of some of these agents are listed below:
antiviral agents: ribavirin and amantadine;
immunomodulatory agents: class I interferons, class 11 interferons and pegylated forms thereof;
HCV polymerase inhibitors: nucleoside analogs and non-nucleosides;
inhibitor of another target in the HCV life cycle that inhibits a target selected from: NS3 helicase, NS2/3 protease or internal ribosome entry site (IRES);
HIV inhibitors: nucleosidic inhibitors, non-nucleosidic inhibitors, protease inhibitors, fusion inhibitors and integrase inhibitors; or
HBV inhibitors: agents that inhibit viral DNA polymerase or is an HBV vaccine.

As discussed above, combination therapy is contemplated wherein a compound of formula (I), or a pharmaceutically acceptable salt thereof, is co-administered with at least one additional agent selected from: an antiviral agent, an immunomodulatory agent, another inhibitor of HCV NS3 protease, an inhibitor of HCV polymerase, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (I), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, in order to prevent the appearance of symptoms of the disease in the individual.

The following sign - - - is used in sub-formulas to indicate the bond, which is connected to the rest of the molecule as defined.

Preferred Embodiments

In the following, the groups, substituents and indices, in particular B, Y, $R^3$, $R^{20}$, $R^{21}$, $R^{22}$, $R^{23}$, $R^{24}$, $R^2$, $R^1$, $R^C$, and $R^S$, are defined as hereinbefore unless stated otherwise.

In the following preferred embodiments, groups and substituents of the compounds according to this invention are described in detail.

According to a preferred embodiment are compounds of formula (I) wherein: Preferably, B is $(C_{2-10})$alkyl, $(C_{3-7})$cycloalkyl, $(C_{1-3})$alkyl-$(C_{3-7})$cycloalkyl or phenyl,
a) wherein said cycloalkyl, alkyl-cycloalkyl and phenyl may be mono-, di- or tri-substituted with $(C_{1-3})$alkyl; and
b) wherein said alkyl, cycloalkyl, alkyl-cycloalkyl and phenyl may be mono- or di-substituted with substituents selected from hydroxy and O—$(C_{1-4})$alkyl; and
c) wherein each of said alkyl-groups and phenyl may be mono-, di- or tri-substituted with fluorine or mono-substituted by chlorine or bromine, and
d) wherein in each of said cycloalkyl-groups being 5-, 6- or 7-membered, one or two —$CH_2$-groups not being directly linked to each other may be replaced by —O— such that the O-atom is linked to the N atom to which B is attached via at least two C-atoms.

Especially preferably, B is $(C_{3-8})$alkyl, $(C_5)$cycloalkyl, or phenyl, wherein each of said groups may be mono- or di-substituted with methyl.

More preferably B is selected from ethyl, n-propyl, i-propyl, n-butyl, 1-methylpropyl, 2-methylpropyl, tert-butyl, cyclopropyl, cyclobutyl, cyclopentyl, cyclohexyl, cyclo-propylmethyl, cyclobutylmethyl, cyclopentylmethyl, cyclohexylmethyl and phenyl;
a) wherein each of said groups optionally being mono-, di- or tri-substituted with substituents selected from methyl and ethyl;
b) wherein each of said groups optionally being mono- or di-substituted with substituents selected from hydroxy, methoxy and ethoxy; and
c) wherein each of said alkyl groups and phenyl may be mono-, di- or tri-substituted with fluorine or mono-substituted by chlorine or bromine; and
d) wherein in all of said cycloalkyl-groups being 5-, 6- or 7-membered, one or two —$CH_2$-groups not being directly linked to each other may be replaced by —O— such that the O-atom is linked to the N atom to which B is attached via at least two C-atoms.

B is most preferably selected from ethyl, 1-methylethyl, 1,1-dimethylethyl, propyl, 1-methylpropyl, 2-methylpropyl, 1,1-dimethylpropyl, 1,2-dimethylpropyl, 2,2-dimethylpropyl, 1,2,2-trimethylpropyl, 1-ethylpropyl, 1-ethyl-2-methylpropyl, 1-(1-methylethyl)-2-methylpropyl, 1-ethyl-2,2-dimethylpropyl, butyl, 1-methylbutyl, 2-methylbutyl, 3-methylbutyl, 1,2-dimethylbutyl, 1,1-dimethylbutyl, 1,3-dimethylbutyl, 2,2-dimethylbutyl, 2,3-dimethylbutyl, 3,3-dimethylbutyl, 1,2,2-trimethylbutyl, 1,2,3-trimethylbutyl, 2,2,3-trimethylbutyl, 2,3,3-trimethylbutyl and 2,2,3-trimethylbutyl, whereby these alkyl-groups may be substituted with chlorine or bromine or 1, 2 or 3 fluorine substituents. Examples of preferred fluorinated alkyl groups include, but are not limited to, 2-fluoroethyl and 3,3,3-trifluoropropyl.

Furthermore most preferably, B is selected from 1,1-dimethylethyl, 1,1-dimethylpropyl, cyclopropyl, cyclobutyl, cyclopentyl, cyclohexyl, cyclopropylmethyl, cyclobutylmethyl, cyclopentylmethyl, cyclohexylmethyl and phenyl; wherein all said groups may be mono- or di-substituted with methyl.

Still most preferably B is selected from 1,1-dimethylethyl, 1,1-dimethylpropyl, cyclopropyl, cyclobutyl, cyclopentyl, cyclohexyl, 1-methylcyclopentyl, 1-methylcyclohexyl and phenyl.

Even most preferably B is selected from 1,1-dimethylethyl, 1,1-dimethylpropyl, cyclopentyl, cyclohexyl and phenyl.

In addition, most preferably B is selected from the following formulas, wherein a $CH_2$-group of a cycloalkyl group is replaced by oxygen:

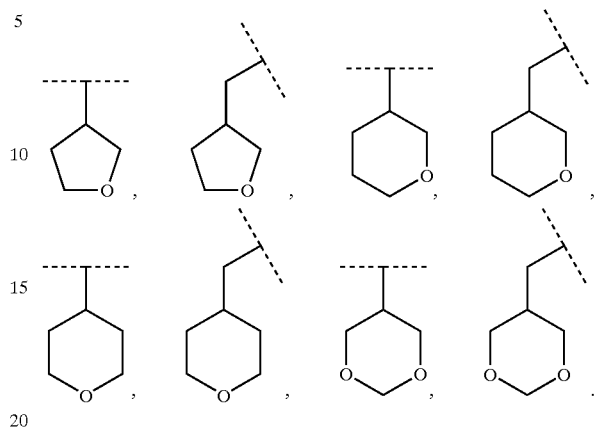

The above listed cycloalkyl and alkyl-cycloalkyl groups, optionally comprising 1 or 2 O-atoms, are optionally substituted by 1, 2 or 3 methyl groups. Especially those cycloalkyl groups, optionally comprising 1 or 2 O-atoms, are preferred, wherein the α-C-atom is substituted with methyl.

Examples of preferred substituted cyclic groups are:

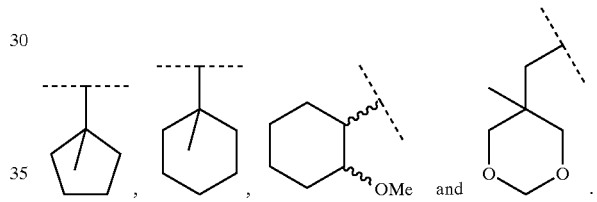

Preferably the substituent Y is defined as H or methyl, in particular H.

$R^3$ is preferably $(C_1)$alkyl, $(C_{3-7})$cycloalkyl or $(C_{1-3})$alkyl-$(C_{3-7})$cycloalkyl, wherein each of said cycloalkyl groups are optionally substituted by 1 to 3 substituents selected from $(C_{1-4})$alkyl.

More preferably, $R^3$ is selected from ethyl, propyl, butyl, cyclopropyl, cyclobutyl, cyclopentyl, cyclohexyl, cyclopropylmethyl, cyclobutylmethyl, cyclopentylmethyl and cyclohexylmethyl, all of which optionally being substituted by 1 or 2 substituents selected from methyl, ethyl and propyl.

Most preferably $R^3$ is selected from 1-methylethyl, 1,1-dimethylethyl, 1-methylpropyl, 2-methylpropyl, 1,1-dimethylpropyl, 1,2-dimethylpropyl, 2,2-dimethylpropyl, cyclopentyl, cyclohexyl, 1-methylcyclopentyl, 1-methylcyclohexyl, cyclopentylmethyl, cyclohexylmethyl, (1-methylcyclopentyl)methyl and (1-methylcyclohexyl)methyl.

$R^3$ is even most preferably selected from 1,1-dimethylethyl, cyclopentyl, cyclohexyl and 1-methylcyclohexyl.

Still, $R^3$ is most preferably selected from 1,1-dimethylethyl and cyclohexyl.

$R^2$ is preferably $R^{20}$, —$NR^{21}R^{22}$, —$NR^{22}COR^{20}$, —$NR^{22}COOR^{20}$ and —$NR^{22}$
wherein
$R^{20}$ is selected from $(C_{1-4})$alkyl, $(C_{3-7})$cycloalkyl and $(C_{1-3})$alkyl-$(C_{3-7})$cycloalkyl, wherein said alkyl, cycloalkyl and alkyl-cycloalkyl may be mono-, di- or tri-substituted with $(C_{1-3})$alkyl; and $R^{21}$ is H or $R^{20}$ as defined above; and $R^{22}$ and $R^{23}$ are independently selected from H and methyl, in particular H.

Very preferably $R^2$ is $R^{20}$, —$NR^{21}R^{22}$—$NR^{22}COR^{20}$—$NR^{22}COOR^{20}$ and —$NR^{22}CONR^{23}R^{21}$, wherein $R^{20}$ is selected from methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl and cyclohexylmethyl; all of which optionally being substituted by 1 to 3 substituents selected from methyl and ethyl; and $R^{21}$ is H or $R^{20}$ as defined above; and $R^{22}$ and $R^{23}$ are independently selected from H and methyl, in particular H.

Most preferably $R^2$ is —$NHR^{21}$ or —$NHCOR^{20}$, wherein $R^{20}$ and $R^{21}$ are defined as hereinbefore.

Preferably, $R^{20}$ and $R^{21}$ are independently selected from: methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl and cyclohexylmethyl all of which optionally being mono- or di-substituted with methyl or ethyl.

$R^2$ is most preferably selected from
a) amino, N-methylamino, N-ethylamino, N-propylamino, N-(1-methylethyl)amino, N-(1,1-dimethylethyl)amino, N-(2-methylpropyl)amino, N-(1-methylpropyl)amino, N-(2,2-dimethylpropyl)amino, N-(1,2-dimethylpropyl)amino, N-(1,1-dimethylpropyl) amino, N-cyclopropylamino, N-cyclobutylamino-, N-cyclopentylamino-, N-cyclohexylamino-, N-(cyclopropylmethyl)amino, N-(cyclobutylmethyl) amino, N-(cyclopentylmethyl)amino, and N-(cyclohexylmethyl)-amino; and
b) methylcarbonylamino, ethylcarbonylamino, 1-methylethylcarbonylamino, propylcarbonylamino, 2-methylpropylcarbonylamino, 1-methylpropylcarbonylamino, 2,2-dimethylpropylcarbonylamino, 1,2-dimethylpropylcarbonylamino, 1,1-dimethylpropylcarbonylamino, cyclopropylcarbonylamino, cyclobutylcarbonylamino, cyclopentylcarbonylamino, cyclohexylcarbonylamino, cyclopropylmethylcarbonylamino, cyclobutylmethylcarbonylamino, cyclopentylmethylcarbonylamino and cyclohexylmethylcarbonylamino;
wherein all said groups may be mono- or disubstituted with methyl.

$R^{24}$ is preferably —$OCH_3$ or —$N(CH_3)_2$. More preferably, $R^{24}$ is —$OCH_3$.

Preferably, $R^1$ is ethyl or vinyl.

Therefore, in the case where $R^1$ is ethyl, the asymmetric carbon atoms in the cyclopropyl group take the R,R configuration according to the sub-formula:

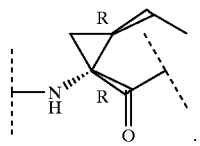

In the case where $R^1$ is vinyl, the asymmetric carbon atoms in the cyclopropyl group take the R,S configuration according to the sub-formula:

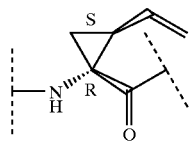

More preferably, $R^1$ is vinyl.

$R^C$ is preferably selected from hydroxy or $NHSO_2R^S$ wherein $R^S$ is methyl, ethyl, n-propyl, i-propyl, n-butyl, 1-methylpropyl, 2-methylpropyl, tert-butyl, cyclopropyl, cyclobutyl, cyclopentyl, cyclohexyl, cyclopropylmethyl, cyclobutylmethyl, cyclopentylmethyl, cyclohexylmethyl, phenyl, naphthyl, pyridinyl, phenylmethyl (benzyl), naphthylmethyl or pyridinylmethyl;

a) all of which optionally being mono-, di- or tri-substituted with substituents selected from fluorine and methyl; and
b) all of which optionally being mono- or disubstituted with substituents selected from hydroxy, trifluoromethyl, methoxy and trifluoromethoxy; and
c) all of which optionally being monosubstituted with substituents selected from chlorine, bromine, cyano, nitro, —$CO$—$NH_2$, —$CO$—$NHCH_3$, —$CO$—$N(CH_3)_2$, —$NH_2$, —$NH(CH_3)$ and —$N(CH_3)_2$.

Most preferably, $R^C$ is hydroxy, $NHSO_2$-methyl, $NHSO_2$-ethyl, $NHSO_2$-(1-methyl)ethyl, $NHSO_2$-propyl, N $HSO_2$-cyclopropyl, N $HSO_2$-cyclopropylmethyl, $NHSO_2$-cyclobutyl, $NHSO_2$-cyclopentyl or $NHSO_2$-phenyl.

According to a most preferred embodiment, the group $R^C$ is hydroxy. According to an alternative most preferred embodiment, the group $R^C$ is $NHSO_2$-cyclopropyl.

Also encompassed within the scope of the present invention, are compounds of formula (I) wherein:

B is $(C_2I_0)$alkyl, $(C_{3-7})$cycloalkyl or $(C_{1-4})$alkyl-$(C_{3-7})$ cycloalkyl,
a) wherein said cycloalkyl and alkyl-cycloalkyl may be mono-, di- or tri-substituted with $(C_{1-3})$alkyl; and
b) wherein said alkyl, cycloalkyl and alkyl-cycloalkyl may be mono- or di-substituted with substituents selected from hydroxy and O—$(C_{1-4})$alkyl; and
c) wherein all said alkyl-groups may be mono-, di- or tri-substituted with halogen; and
d) wherein in said cycloalkyl-group being 5-, 6- or 7-membered, one or two —$CH_2$-groups not being directly linked to each other may be replaced by —O— such that the O-atom is linked to the N atom to which B is attached via at least two C-atoms; or B is phenyl, $(C_{1-3})$alkyl-phenyl, heteroaryl or $(C_{1-3})$alkyl-heteroaryl, wherein the heteroaryl-groups are 5- or 6-membered having from 1 to 3 heteroatoms selected from N, O and S; wherein said phenyl and heteroaryl groups may be mono-, di- or trisubstituted with substituents selected from halogen, —OH, $(C_{1-4})$alkyl, O—$(C_{1-4})$alkyl, S—$(C_{1-4})$alkyl, —$NH_2$, —$NH((C_{1-4})$alkyl) and —$N((C_{1-4})$alkyl$)_2$, —$CONH_2$ and —$CONH$—$(C_{1-4})$alkyl;

Y is H or $(C_1)$alkyl;

$R^3$ is $(C_1)$alkyl, $(C_{3-7})$cycloalkyl or $(C_{1-3})$alkyl-$(C_{3-7})$ cycloalkyl, wherein said cycloalkyl groups may be mono-, di- or tri-substituted with substituents selected from halogen, —OH, $(C_{1-4})$alkyl, O—$(C_{1-4})$alkyl, S—$(C_{1-4})$alkyl, —$NH_2$, —$NH((C_{1-4})$alkyl) and —$N((C_{1-4})$alkyl$)_2$, —COOH and —$CONH_2$;

$R^2$ is $R^{20}$ is $NR^{21}R^{22}$—$NR^{22}COR^{20}$, —$NR^{22}COOR^{20}$ and —$NR^{22}CONR^{23}R^{21}$, wherein $R^{20}$ is selected from $(C_{1-8})$alkyl, $(C_{3-7})$cycloalkyl and $(C_{1-4})$alkyl-$(C_{3-7})$cycloalkyl, wherein said cycloalkyl and alkyl-cycloalkyl may be mono-, di- or tri-substituted with $(C_{1-3})$alkyl; and $R^{21}$ is H or $R^{20}$, $R^{22}$ and $R^{23}$ are independently selected from H and methyl, and $R^{24}$ is selected from: —O—$(C_{1-4})$alkyl, NH($(C_{1-4})$alkyl) and —N($(C_{1-4})$alkyl)$_2$;

$R^1$ is $(C_1)$alkyl or $(C_{2-6})$alkenyl; and $R^C$ is hydroxy or $NHSO_2R^S$ wherein $R^S$ is $(C_1)$alkyl, $(C_{3-7})$cycloalkyl or $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; all of which being optionally mono-, di- or tri-substituted with substituents selected from halogen, hydroxy, cyano, $(C_{1-4})$alkyl, O—$(C_1)$alkyl, —CO—$NH_2$, —CO—NH ($(C_{1-4})$alkyl), —CO—N($(C_{1-4})$alkyl)$_2$, —$NH_2$, —NH ($(C_{1-4})$alkyl) and —N($(C_{1-4})$alkyl)$_2$; and all of which optionally being monosubstituted with nitro;

or a pharmaceutically acceptable salt or ester thereof.

Preferably,

B is $(C_{3-8})$alkyl, $(C_{5-6})$cycloalkyl, or phenyl, all said groups being optionally mono- or di-substituted with methyl;

Y is H or methyl;

$R^3$ is $(C_{1-6})$alkyl or $(C_{3-7})$cycloalkyl, said cycloalkyl being optionally substituted by 1 to 3 substituents selected from $(C_{1-4})$alkyl;

$R^2$ is $R^{20}$, —$NR^2R^{22}$, —$NR^{22}COR^{20}$, —$NR^{22}COOR^{20}$ and —$NR^{22}CONR^{23}R^{21}$, wherein $R^{20}$ is selected from methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, cyclopropyl-methyl, cyclobutyl-methyl, cyclopentyl-methyl and cyclohexyl-methyl, all of which optionally being substituted by 1 to 3 substituents selected from methyl and ethyl;

$R^{21}$ is H or $R^{20}$ as defined above;

$R^{22}$ and $R^{23}$ are independently selected from H and methyl;

$R^{24}$ is —$OCH_3$ or —$N(CH_3)_2$;

$R^1$ is ethyl or vinyl; and $R^C$ is hydroxy, $NHSO_2$-methyl, $NHSO_2$-ethyl, $NHSO_2$-(1-methyl)ethyl, $NHSO_2$-propyl, $NHSO_2$-cyclopropyl, $NHSO_2$-cyclopropylmethyl, $NHSO_2$-cyclobutyl, $NHSO_2$-cyclopentyl or $NHSO_2$-phenyl.

More preferably, B is selected from 1,1-dimethylethyl, 1,1-dimethylpropyl, cyclopropyl, cyclobutyl, cyclopentyl, cyclohexyl, 1-methylcyclopentyl, 1-methylcyclohexyl and phenyl; Y is H; $R^3$ is selected from 1,1-dimethylethyl, cyclopentyl, cyclohexyl and 1-methylcyclohexyl; $R^2$ is —$NHR^{21}$ or —$NHCOR^{20}$, wherein $R^{20}$ and $R^{21}$ are independently selected from: methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, all of which optionally being mono- or di-substituted with methyl or ethyl; $R^{24}$ is —$OCH_3$; $R^1$ is vinyl and $R^C$ is hydroxy or $NHSO_2$-cyclopropyl.

Most preferably, B is selected from 1,1-dimethylethyl, 1,1-dimethylpropyl, cyclopentyl, cyclohexyl and phenyl; $R^3$ is selected from 1,1-dimethylethyl and cyclohexyl; and $R^C$ is hydroxy.

Examples of preferred compounds according to this invention are contained in Table 1.

According to an alternate embodiment, the pharmaceutical composition of this invention may additionally comprise at least one other anti-HCV agent. Examples of anti-HCV agents include, but are not limited to, α-(alpha), β-(beta), δ-(delta), γ-(gamma), ω-(omega) and tau-interferon, pegylated α-interferon, ribavirin and amantadine.

According to another alternate embodiment, the pharmaceutical composition of this invention may additionally comprise at least one other inhibitor of HCV NS3 protease.

According to another alternate embodiment, the pharmaceutical composition of this invention may additionally comprise at least one inhibitor of HCV polymerase. According to yet another alternate embodiment, the pharmaceutical composition of this invention may additionally comprise at least one inhibitor of other targets in the HCV life cycle, including but not limited to, helicase, NS2/3 protease or internal ribosome entry site (IRES).

The pharmaceutical composition of this invention may be administered orally, parenterally or via an implanted reservoir. Oral administration or administration by injection is preferred. The pharmaceutical composition of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, and intralesional injection or infusion techniques.

The pharmaceutical composition may be in the form of a sterile injectable preparation, for example, as a sterile injectable aqueous or oleaginous suspension. This suspension may be formulated according to techniques known in the art using suitable dispersing or wetting agents (such as, for example Tween 80) and suspending agents.

The pharmaceutical composition of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

Other suitable vehicles or carriers for the above noted formulations and compositions can be found in standard pharmaceutical texts, e.g. in "Remington's Pharmaceutical Sciences", The Science and Practice of Pharmacy, 19$^{th}$ Ed. Mack Publishing Company, Easton, Pa., (1995).

Dosage levels of between about 0.01 and about 100 mg/kg body weight per day, preferably between about 0.1 and about 50 mg/kg body weight per day of the protease inhibitor compound described herein are useful in a monotherapy for the prevention and treatment of HCV mediated disease. Typically, the pharmaceutical composition of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician. Generally, treatment is initiated with small dosages substantially less than the optimum dose of the peptide. Thereafter, the dosage is increased by small increments until the optimum effect under the circumstances is reached. In general, the compound is most desirably administered at a concentration level that will generally afford antivirally effective results without causing any harmful or deleterious side effects.

When the composition of this invention comprises a combination of a compound of formula I, including a pharmaceutically acceptable salt or ester thereof, and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts and esters are formulated together with a pharmaceutically acceptable carrier, the resulting composition may be administered in vivo to mammals, such as man, to inhibit HCV NS3 protease or to treat or prevent HCV virus infection. Such treatment may also be achieved using a compound of this invention in combination with another antiviral agent. Preferred other antiviral agents are described within the Definitions section and the section of preferred pharmaceutical compositions according to this invention and include, but are not limited to: α-, β-, δ-, ω-, γ-and tau-interferon, ribavirin, amantadine; other inhibitors of HCV NS3 protease; inhibitors of HCV polymerase; inhibitors of other targets in the HCV life cycle, which include but are not limited to, helicase, NS2/3 protease, or internal ribosome entry site (IRES); or combinations thereof. The additional agents may be combined with compounds of this invention to create a single dosage form. Alternatively these additional agents may be separately administered to a mammal as part of a multiple dosage form.

Accordingly, another embodiment of this invention provides a method of inhibiting HCV NS3 protease activity in a mammal by administering a compound of the formula I, including a pharmaceutically salt or ester thereof.

In a preferred embodiment, this method is useful in decreasing the NS3 protease activity of the hepatitis C virus infecting a mammal.

As discussed above, combination therapy is contemplated wherein a compound of formula (I), or a pharmaceutically acceptable salt or ester thereof, is co-administered with at least one additional antiviral agent. Preferred antiviral agents are described hereinbefore and examples of such agents are provided in the Definitions section. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt or ester thereof.

A compound of formula (I), or a pharmaceutically acceptable salt or ester thereof, set forth herein may also be used as a laboratory reagent. Furthermore a compound of this invention, including a pharmaceutically acceptable salt or ester thereof, may also be used to treat or prevent viral contamination of materials and therefore reduce the risk of viral infection of laboratory or medical personnel or patients who come in contact with such materials (e.g. blood, tissue, surgical instruments and garments, laboratory instruments and garments, and blood collection apparatuses and materials).

A compound of formula (I), including a pharmaceutically acceptable salt or ester thereof, set forth herein may also be used as a research reagent. A compound of formula (I), including a pharmaceutically acceptable salt or ester thereof, may also be used as positive control to validate surrogate cell-based assays or in vitro or in vivo viral replication assays.

Succinic Acid Moieties

In another aspect of the present invention, there is provided a process for the preparation of a succinamide peptide analog of formula (I) comprising the steps of coupling a peptide of the formula (III):

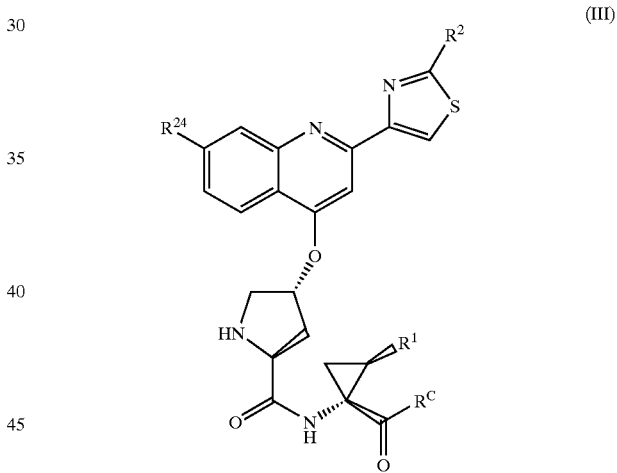

(III)

wherein $R^C$ is —O-CGP or —NHSO$_2$R$^S$; and $R^1$ and $R^S$ are as defined hereinbefore and CPG is a carboxylprotecting group;
with a succinic acid moiety of formula (II):

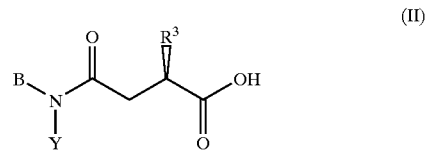

(II)

wherein B, Y and $R^3$ are as defined hereinbefore.

Use of the succinic acid moiety of the formula (II) in the preparation of a peptide analog of formula (I), is likewise provided.

Preferably the groups and substituents B, Y, $R^3$, $R^{24}$, $R^2$, $R^1$ and $R^S$, are defined according to one or more of the preferred embodiments as described hereinbefore.

Methodologies
Linking of Moieties

The compounds of the present invention are synthesized according to a general process as illustrated in Scheme I (wherein CPG is a carboxylprotecting group and APG is an amino protecting group):

SCHEME I

P1-OH ⟶ P1-O-CPG $\xrightarrow{\text{+ APG-P2-OH}}$

APG-P2-P1-O-CPG ⟶ P2-P1-O-CPG $\xrightarrow{\text{+ succinic acid moiety}}$ succinamide-P2-P1-O-CPG ⟶ succinamide-P2-P1-OH (of formula I)

wherein the succinic acid moiety is

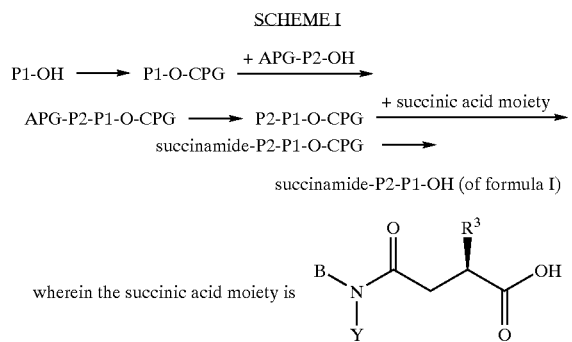

Details respecting the protocols used to prepare, in part, compounds and intermediates of the present invention are detailed in WO 99/07733, WO 00/09558, WO 00/09543, and WO 00/59929.

Briefly, the P1, P2, and succinic acid moieties can be linked by well known peptide coupling techniques. The P1 and P2 groups and the succinic acid moiety may be linked together in any order as long as the final compound corresponds to peptide analogs of Formula (I). For example, the succinic acid moiety can be linked to P2-P1; or P1 linked to an succinamide-P2 fragment.

Generally, peptides are elongated by deprotecting the α-amino group of the N-terminal residue and coupling the unprotected carboxyl group of the next suitably N-protected amino acid through a peptide linkage using the methods described. This deprotection and coupling procedure is repeated until the desired sequence is obtained. This coupling can be performed with the constituent amino acids and succinic acid moiety in stepwise fashion, as depicted in Scheme I, or by solid phase peptide synthesis according to the method originally described in Merrifield, J. Am. Chem. Soc., (1963), 85, 2149–2154.

Coupling between two amino acids, an amino acid and a peptide or the succinic acid moiety, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole. These coupling reactions can be performed in either solution (liquid phase) or solid phase.

More explicitly, the coupling step involves the dehydrative coupling of a free carboxyl of one reactant with the free amino group of the other reactant in the presence of a coupling agent to form a linking amide bond. Descriptions of such coupling agents are found in general textbooks on peptide chemistry, for example, M. Bodanszky, "Peptide Chemistry", $2^{nd}$ rev ed., Springer-Verlag, Berlin, Germany, (1993). Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy)tris-(dimethylamino)phosphonium hexafluorophosphate, either by itself or in the presence of 1-hydroxybenzotriazole. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotriazol-1-yl)-N,N,N',N'-tetramethyluronium hexafluorophosphate. The coupling reaction is conducted in an inert solvent, e.g. dichloromethane, acetonitrile or dimethylformamide. An excess of a tertiary amine, e.g. diisopropylethylamine, N-methylmorpholine or N-methylpyrrolidine, is added to maintain the reaction mixture at a pH of about 8. The reaction temperature usually ranges between 0° C. and 50° C. and the reaction time usually ranges between 15 min and 24 h.

When a solid phase synthetic approach is employed, the C-terminal carboxylic acid is attached to an insoluble carrier (usually polystyrene). These insoluble carriers contain a group that will react with the carboxylic group to form a bond that is stable to the elongation conditions but readily cleaved later. Examples of which are: chloro- or bromomethyl resin, hydroxymethyl resin, trytil resin and 2-methoxy-4-alkoxy-benzylaloconol resin.

The functional groups of the constituent amino acids generally must be protected during the coupling reactions to avoid formation of undesired bonds. The protecting groups that can be used are listed in Greene et al., "Protective Groups in Organic Synthesis", John Wiley & Sons, New York (1991) and "The Peptides: Analysis, Synthesis, Biology", Vol. 3, Academic Press, New York (1981), the disclosures of which are hereby incorporated by reference.

The α-carboxyl group of the C-terminal residue is usually protected as an ester (CPG) that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

The α-amino group of each amino acid to be coupled to the growing peptide chain must be protected (APG). Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. The preferred α-amino protecting group is either Boc or Fmoc. Many amino acid derivatives suitably protected for peptide synthesis are commercially available.

The α-amino protecting group of the newly added amino acid residue is cleaved prior to the coupling of the next amino acid. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature (RT) usually 20–22° C.

Compounds of formula I wherein $R^C$ is $NHSO_2R^S$ as defined herein are prepared by coupling the corresponding acid of formula I (i.e. $R^C$ is hydroxy) with an appropriate sulfonamide of formula $R^SSO_2NH_2$ in the presence of a coupling agent under standard conditions. Although several commonly used coupling agents can be employed, TBTU and HATU have been found to be practical. The sulfonamides are available commercially or can be prepared by known methods.

Synthesis of Succinic Acid Moieties

Different succinic acid moieties may be prepared in the following manner: Nucleophilic attack of an amine with a succinic anhydride analog:

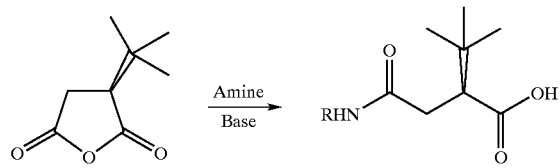

Tert-butyl succinic anhydride is reacted with a primary amine in the presence of a base such as pyridine at temperatures ranging from about −40 to 25° C. to yield the desired succinic acid fragment (P. Beaulieu, et al., J. Med. Chem. 1997, 40, 2164–2176).

Alternatively, the succinic acid moieties can be prepared via Evans alkylation as described by D. A. Evans et al., J. Org. Chem. 1999, 40 (17), 6411–6417 and also by R. Beckett et al., Synlett 1993, 2,137–138.

Synthesis of P2 Moieties

The synthesis of the P2 moieties used for the synthesis of formula (I) are described in WO 00/59929, which in turn incorporates the teachings of WO 00/09558 and WO 00/09543.

Synthesis of P1 Moieties

The synthesis of the P1 moieties used for the synthesis of formula (I) are described in WO 00/59929, which in turn incorporates the teachings of WO 00/09558 and WO 00/09543.

EXAMPLES

The present invention is illustrated in further detail by the following non-limiting examples. Other specific ways of synthesis or resolution can be found in WO 00/59929, WO 00/09558 and WO 00/09543.

Temperatures are given in degrees Celsius. Solution percentages express a weight to volume relationship, and solution ratios express a volume to volume relationship, unless stated otherwise. Nuclear magnetic resonance (NMR) spectra were recorded on a Bruker 400 MHz spectrometer; the chemical shifts (δ) are reported in parts per million. Flash chromatography was carried out on silica gel ($SiO_2$) according to Still's flash chromatography technique (W. C. Still et al., J. Org. Chem., (1978), 43, 2923).

Abbreviations used in the examples include

Bn: benzyl; Boc: tert-butyloxycarbonyl {$Me_3COC(O)$}; BSA: bovine serum albumin; DCM: dichloromethane; DIPEA: diisopropylethylamine; DCC: 1,3-dicyclohexylcarbodiimide; DME: 1,2-dimethyoxyethane; DMF: dimethylformamide; DMSO: dimethylsulfoxide; EDTA: ethylenediaminetetraacetic acid; Et: ethyl; EtOH: ethanol; EtOAc: ethyl acetate; $Et_2O$: diethyl ether; HATU: [0-7-azabenzotriazol-1-yl)-1,1,3,3-tetramethyluronium hexafluorophosphate]; HPLC: high performance liquid chromatography; MS: mass spectrometry (MALDI-TOF: Matrix Assisted Laser Desorption Ionization-Time of Flight, FAB: Fast Atom Bombardment); LAH: lithium aluminum hydride; Me: methyl; MeOH: methanol; MES: (2-{N-morpholino}ethane-sulfonic acid); Pr: propyl; Succ: 3-carboxypropanoyl; PNA: 4-nitrophenylamino or p-nitroanilide; TBAF: tetra-n-butylammonium fluoride; TBTU: 2-(1H-benzotriazole-1-yl)-1,1,3,3-tetramethyluronium tetrafluoroborate; TFA: trifluoroacetic acid; THF: tetrahydrofuran; TIS: triisopropylsilane; TLC: thin layer chromatography; Tris/HCl: tris(hydroxymethyl)aminomethane hydrochloride.

P1 and P2 Building Blocks

P1 and P2 moieties of compounds of Formula (I) are prepared using the protocols outlined in WO 00/59929, published Oct. 12, 2000, and WO 00/09543, published on Feb. 24, 2000.

In particular, reference is made to pages 33–35, Example 1 of WO 00/59929.

Furthermore, of the WO 00/09543 reference is made to:

the General Methods section (pages 32 to 36), the synthesis of P2 moieties on the pages 39 to 42, the synthesis of P1 moieties on the pages 42 to 48, the synthesis methods in the Examples section (pages 48 to 92), especially to the pages 56–69, Examples 9 to 20 for the preparation of 1-aminocyclopropylcarboxylic acid P1 moieties.

Succinic Acid Building Blocks and Intermediates

General procedure for the preparation of (S)-2-tert-Butylsuccinic $N^4$-Amides (Regioselective Anhydride Opening)

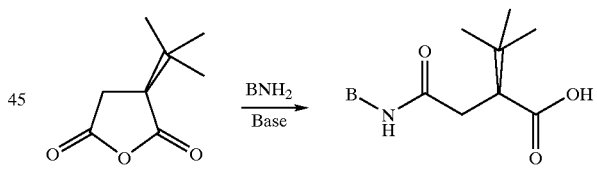

The (S)-2-tert-Butylsuccinic Anhydride was prepared according to literature methods [P. Beaulieu et. al., J. Med. Chem. 1997, 40 (14), 2164–2176 and S. Widequist, Ark. Kemi. 1950, 2, 321; Chem. Abstr. 1951, 45, 2870a and T. Polonski, J. Chem. Soc. Perkin Trans.1, 1988, 629–637.]

The (S)-2-tert-butylsuccinic anhydride (1 equiv) was dissolved in pyridine and the solution cooled to −40° C. (dry ice/acetone). The amine $B-NH_2$ (1.2 equiv), wherein the substituent B is defined as in claim 1, in pyridine was added dropwise and the mixture stirred for 10 min. The cooling bath was removed and the solution stirred overnight at room temperature. Pyridine and excess amine were evaporated under vacuum, and the oily residue was dissolved in EtOAc. The solution was washed successively with 20% aqueous citric acid (4×) and brine (2×) and then dried over $MgSO_4$. Removal of volatiles under reduced pressure and purification by crystallization or flash chromatography gave desired amides usually as white solids.

General Procedure for the Preparation of (±)-2-Cyclohexylsuccinic N⁴-Amides (Regioselective Anhydride Opening)

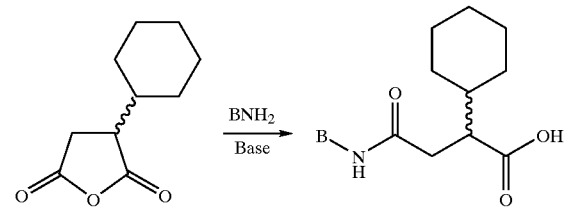

Racemic 2-cyclohexylsuccinic anhydride was prepared from commercially available (±)-2-cyclohexylsuccinic acid. [J. Am. Chem. Soc. 1940, 62, 2450–2454].

Briefly, the (±)-cyclohexylsuccinic acid (10 g, 0.05 mol) was dissolved in acetic anhydride (100 mL) and heated at 54° C. for 1 h and then stirred 16 hours at RT. The mixture was concentrated in vacuo and then placed under high vacuum. A portion of this material (0.53 g, 2.9 mmol) was opened with an amine B-NH$_2$, for example cyclopentylamine (0.34 mL, 3.5 mmol), as described above to give the expected product.

For the product (±)-2-Cyclohexylsuccinic N⁴-Cyclopentylamide the following physicochemical data were obtained:

MS (electrospray): (M−H)−; 266.0 and (M+H)+; 268.1. ¹H NMR (400 MHz, DMSO-d$_6$) δ 12.0 (bs, 1H), 7.76 (d, J=7 Hz, 1H), 4.0–3.85 (m, 1H), 2.34 (dd, J=9.5, 9.5 Hz, 1H), 2.16 (dd, J=5, 5 Hz, 1H), 2.68–2.50 (m, 1H), 1.80–1.53 (m, 9H), 1.52–1.40 (m, 3H), 1.39–1.27 (m, 2H), 1.24–0.93 (m, 5H).

General Method of Coupling of the Succinic Amide Moiety with a Dipeptide

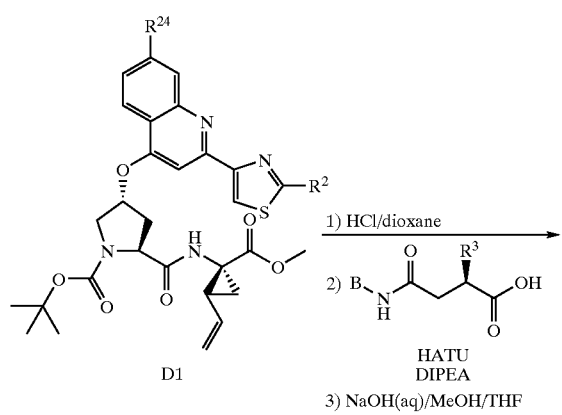

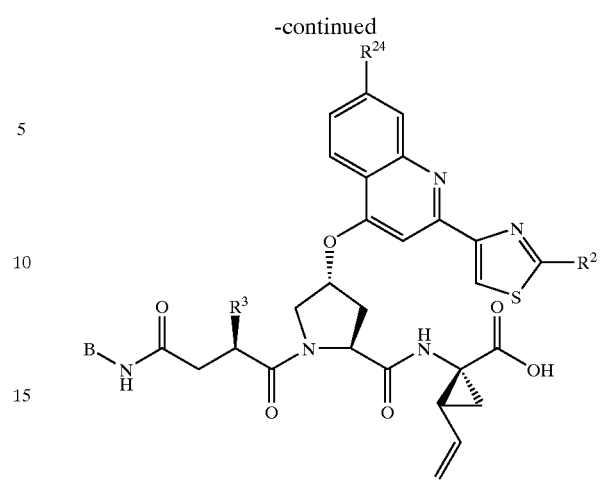

The Boc-dipeptide of the formula D1 wherein the substituent R$^2$ is CH$_3$CONH— and the substituent R$^{24}$ is —OCH$_3$ can be obtained by the synthesis method as described in the Examples section of WO 00/09543, in particular according to the synthesis of compound 35n in Example 35 therein.

The Boc-dipeptide D1 wherein the substituent R$^2$ is CH$_3$CONH— and the substituent R$^{24}$ is —OCH$_3$ (50 mg, 0.077 mmol) was dissolved in 4N HCl/dioxane (2 mL) and stirred for 30 minutes at RT. The solvent was removed under reduced pressure to give the deprotected HCl salt. The salt was dried under high vacuum before coupling. The dried HCl salt of the dipeptide was dissolved in DMF (2 mL) and then treated with HATU (35 mg, 0.092 mmol), the succinic acid moiety (0.092 mmol), and DIPEA (51 μL, 0.40 mmol, 4.3 equiv). The mixture was stirred 48 hours before being concentrated to dryness. The material was purified by preparative HPLC.

In the case of (S)-2-tert-butylsuccinic N⁴-cyclohexylamide as the succinic acid moiety a pale yellow solid was obtained: 54 mg (89%) of 98% homogeneity by analytical HPLC analysis. MS (electrospray), (M−H)−; 787.3 and (M+H)+; 789.4.

According to the step 3) of the above scheme, the P1 ester is hydrolyzed by dissolving the purified succinamide dipeptide (54 mg according to the above example) in methanol (1.5 mL), THF (1.5 mL) and distilled water (1 mL) before being treated with 1N NaOH (aq) solution (0.70 mL, 10 equiv.). The homogeneous solution was stirred 16 hours and then concentrated to dryness. The crude material was dissolved in DMSO (2 mL) and purified by preparative HPLC.

Alternative Approach for the Preparation of a (S)-2-Tert-Butylsuccinic Acid Moiety A general method for the synthesis of enantiomerically pure α-substituted succinic acid derivatives has been described by D. Evans et. al., J. Org. Chem. 1999, 64(17), 6411–6417.

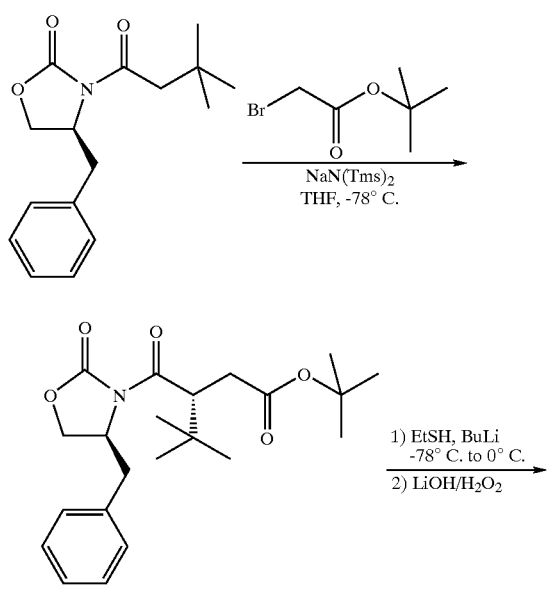

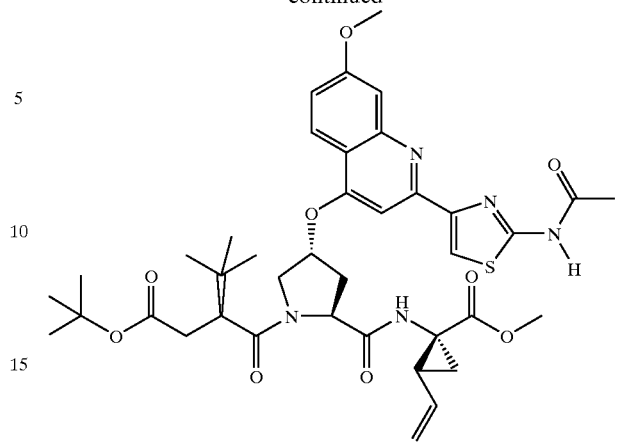

The tert-butyl ester can be cleaved with HCl/dioxane to liberate the terminal acid which can then be readily coupled with a variety of primary amines B-NH$_2$. Hydrolysis of the P1 methyl ester group delivers the final product:

According to this approach, the oxazolidinone analog of tert-butylacetic acid is alkylated stereoselectively with tert-butyl bromoacetate at low temperature with a strong base to yield the enantiomerically pure succinate derivative. Removal of the chiral auxillary leads to the desired succinate analog. This succinate ester can be coupled to the dipeptide fragment D1 wherein the substituent R$^2$ is CH$_3$CONH— and the substituent R$^{24}$ is —OCH$_3$, using the coupling protocols as described hereinbefore and hereinafter to give the tert-butyl ester protected coupled succinate as shown in the reaction scheme:

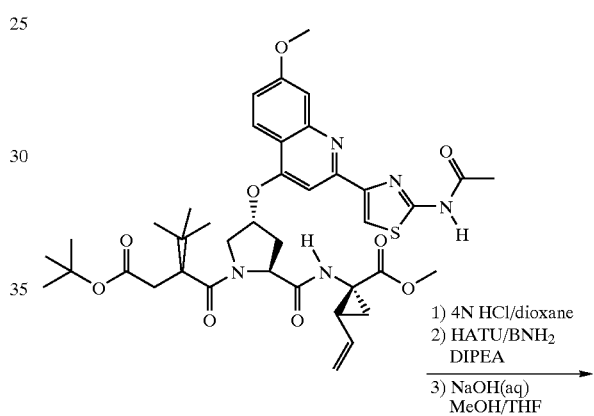

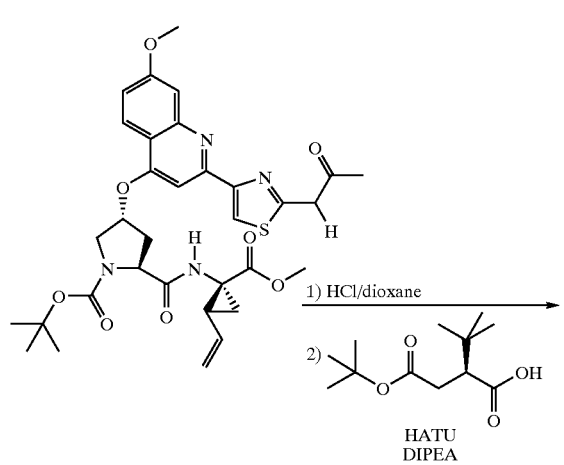

Example 1

Synthesis of Compound 11 (of Table 1)

According to the above described general method a succinic acid amide moiety, with B being tert-butyl and R$^3$ being tert-butyl, is coupled with the Boc-dipeptide D1 wherein the substituent $R^2$ is $CH_3CONH$— and the substituent $R^{24}$ is —$OCH_3$ as described above.

The saponified material was purified by preparative HPLC (37 mg, 48% over 2 steps). HPLC (purity)=96%; MS (electrospray), (M–H)–; 747.3 and (M+H)$^+$; 749.3. $^1$H NMR (400 MHz, DMSO-d$_6$) δ 12.47 (s, 1H), 8.59 (s, 1H), 8.42 (d, J=9 Hz, 1H), 7.75–7.56 (m, 2H), 7.31 (s, 1H), 7.23–7.17 (m, 1H), 5.8–5.67 (m, 1H), 5.65–5.52 (m, 1H), 5.17 (d, J=18.4 Hz, 1H), 5.05 (d, J=11.9 Hz, 1H), 4.50 (bd, J=11.3 Hz, 1H), 4.36 (dd, J=9.4 and 7.6 Hz, 1H), 4.07–3.97 (m, 2H), 3.96 (s, 3H), 2.68–2.62 (m, 1H), 2.38–2.27 (m, 1H), 2.23 (s, 3H), 2.22–2.14 (m, 1H), 2.03 (dd, J=8.6, and 8.6 Hz, 1H), 1.53 (dd, J=9.4 and 9.4 Hz, 1H), 1.22 (bs, 1H), 1.02 (bs, 9H), 0.94 (s, 9H), 0.90–0.85 (m, 2H).

Example 2

Synthesis of Compound 12

According to the above described general method a succinic acid amide moiety, with B being cyclopentyl and $R^3$ being tert-butyl, is coupled with the Boc-dipeptide D1 wherein the substituent $R^2$ is $CH_3CONH$— and the substituent $R^{24}$ is —$OCH_3$ as described above.

The saponified material was purified by preparative HPLC (5.5 mg, 12% over 2 steps). HPLC (purity)=96.5%; MS (electrospray), (M–H)–; 759.3 and (M+H)+; 761.3. $^1$H NMR (400 MHz, DMSO-d$_6$) δ 12.4 (s, 1H), 8.60 (s, 1H), 8.45 (s, 1H), 8.38 (d, J=9.2 Hz, 1H), 7.66 (s, 1H), 7.62 (d, J=7.2 Hz, 1H), 7.52 (s, 1H), 7.21 (d, J=7.2 Hz, 1H), 5.78–5.64 (m, 1H), 5.58 (bs, 1H), 5.17 (d, J=17 Hz, 1H), 5.05 (d, J=9.6 Hz, 1H), 4.58–4.50 (m, 1H), 4.41–4.32 (m, 1H), 3.95 (s, 3H), 2.73–2.65 (m, 2H), 2.46–2.37 (m, 1H), 2.35–2.25 (m, 1H), 2.23 (s, 3H), 2.14–1.91 (m, 2H), 1.57–1.40 (m, 5H), 1.37–1.21 (m, 3H), 1.21 (bs, 1H), 1.17–1.10 (m, 1H), 0.91 (s, 9H), 0.88–0.79 (m, 2H).

Example 3

Synthesis of Compound 13

According to the above described general method a succinic acid amide moiety, with B is cyclohexyl and $R^3$ is tert-butyl, is coupled with the Boc-dipeptide D1 wherein the substituent $R^2$ is $CH_3CONH$— and the substituent $R^{24}$ is —$OCH_3$ as described above.

27.2 mg (53%) of a pale yellow solid was obtained after lyophilization.

HPLC (purity)=100%; MS (electrospray), (M–H)–; 773.3 and (M+H)+; 775.4. $^1$H NMR (400 MHz, DMSO-d$_6$) δ 12.47 (s, 1H), 8.56 (s, 1H), 8.44 (d, J=8.4 Hz, 1H), 7.6 (bs, 1H), 7.56 (d, J=7.6 Hz, 2H), 7.21 (bs, 1H), 5.8–5.68 (m, 1H), 5.55 (bs, 1H), 5.18 (d, J=17 Hz, 1H), 5.04 (d, J=11 Hz, 1H), 4.55 (bd, J=9.7 Hz, 1H), 4.34 (dd, J=7.3, 7.3 Hz, 1H), 3.95 (s, 3H), 3.23–3.1 (m, 1H), 2.79–2.72 (m, 1H), 2.34–2.28 (m, 1H), 2.23 (s, 3H), 2.20–2.13 (m, 1H), 1.61-1.45 (m, 6H), 1.32–1.20 (m, 3H), 1.50–1.0 (m, 4H), 0.95 (s, 9H), 0.89–0.82 (m, 2H).

Example 4

Synthesis of Compound 14

According to the above described general method a succinic acid amide moiety, with B being phenyl and $R^3$ being tert-butyl, is coupled with the Boc-dipeptide D1 wherein the substituent $R^2$ is $CH_3CONH$— and the substituent $R^{24}$ is —$OCH_3$ as described above.

The saponified material was purified by preparative HPLC (14.1 mg, 65%). HPLC (purity)=100%; MS (electrospray), (M–H)–; 767.3 and (M+H)+; 769.4. $^1$H NMR (400 MHz, DMSO-d$_6$) δ 12.4 (s. 1H), 9.85 (s, 1H), 8.5 (s, 1H), 8.15 (d, J=8 Hz, 1H), 7.7–7.6 (m, 2H), 7.3 (d, J=7.6 Hz, 1H), 7.1 (m, 2H), 6.9 (d, J=8 Hz, 1H), 6.8 (d, J=7.6 Hz, 1H), 5.8–5.7 (m, 1H), 5.6–5.5 (bs, 1H), 5.2 (d, J=17 Hz, 1H), 5.0 (d, J=11 Hz, 1H), 4.6–4.5 (m, 1H), 4.3–4.2 (m, 1H), 4.0 (d, J=9 Hz, 1H), 3.95 (s, 3H), 2.95–2.7 (m, 2H), 2.3–2.2 (m, 1H), 2.2 (s, 3H), 2.0 (dd, J.=8.6 and 8.6 Hz, 1H), 1.6 (m, 1H), 1.25 (m, 1H), 1.0 (s, 9H).

Example 5

Synthesis of Compound 15

According to the above described general method a succinic acid amide moiety, with B being 1,1-dimethylpropyl and $R^3$ being tert-butyl, is coupled with the Boc-dipeptide D1 wherein the substituent $R^2$ is $CH_3CONH$— and the substituent $R^{24}$ is —$OCH_3$ as described above.

The saponified material was purified by preparative HPLC (7 mg, 33% over 2 steps). HPLC (purity)=97%; MS (electrospray), (M–H)–; 761.4 and (M+H)+; 763.4. $^1$H NMR (400 MHz, DMSO-d$_6$) δ 12.45 (s, 1H), 8.58 (s, 1H), 8.37 (d, J=9 Hz, 1H), 7.7–7.4 (m, 2H), 7.25–7.17 (m, 1H), 7.15 (s, 1H), 5.80–5.68 (m, 1H), 5.6–5.5 (m, 1H), (d, J=17 Hz, 1H), 5.04 (d, J=9.6 Hz, 1H), 4.50–4.42 (m, 1H), 4.40–4.33 (m, 1H), 4.02–3.96 (m, 2H), 3.95 (s, 3H), 2.69–2.62 (m, 1H), 2.37–2.28 (m, 1H), 2.22 (s, 3H), 2.08–1.97 (m, 2H), 1.57–1.50 (m, 1H), 1.48–1.34 (m, 2H), 1.32–1.27 (m, 1H), 1.23 (bs, 3H), 1.06–0.97 (bs, 6H), 0.95 (s, 9H), 0.90–0.83 (m, 1H), 0.63 (t, J=7 and 7 Hz, 3H).

Example 6

Synthesis of Compound 16

According to the above described general method a succinic acid amide moiety, with B being cyclopentyl and $R^3$ being cyclohexyl, is coupled with the Boc-dipeptide D1 wherein the substituent $R^2$ is $CH_3CONH$— and the substituent $R^{24}$ is —$OCH_3$ as described above.

The saponified material was purified by preparative HPLC (0.4 mg, 10% over 2 steps). HPLC (purity)=100%; MS (electrospray), (M–H)—; 759.3 and (M+H)+; 761.3.

Example 7

Synthesis of Compound 17

According to the above described general method a succinic acid amide moiety, with B being cyclopentyl and $R^3$ being tert-butyl, is coupled with a Boc-dipeptide D1, wherein the substituent $R^2$ is cyclopentylamino- and the substituent $R^{24}$ is —$OCH_3$ as described above.

The saponified material was purified by preparative HPLC (6 mg, 21% over 2 steps). HPLC (purity)=100%; MS (electrospray), (M–H)–; 785.4 and (M+H)$^+$; 787.4. $^1$H NMR (400 MHz, DMSO-d$_6$) δ 8.59 (s, 1H), 8.40 (d, J=9.0 Hz, 1H), 8.23–8.10 (m, 1H), 7.90–7.68 (m, 2H), 7.62 (d, J=7.0 Hz, 1H), 7.33–7.20 (m, 1H), 5.79–5.67 (m, 1H), 5.68–5.62 (m, 1H), 5.19 (d, J=17 Hz, 1H), 5.06 (d, J=12.0 Hz, 1H), 4.55 (d, J=11.3 Hz, 1H), 4.42–4.35 (m, 1H), 4.34–4.21 (m, 1H), 3.96 (s, 3H), 3.96–3.91 (m, 1H), 2.72–2.65 (m, 1H), 2.45–2.30 (m, 2H), 2.16–2.07 (m, 1H), 2.06–1.97 (m, 3H), 1.79–1.67 (m, 2H), 1.66–1.40 (m, 10H), 1.38–1.21 (m, 4H), 1.20–1.06 (m, 1H), 0.93 (s, 9H), 0.91–0.83 (m, 2H).

Example 8

Synthesis of Compound 18

According to the above described general method a succinic acid amide moiety, with B being phenyl and $R^3$ being tert-butyl, is coupled with a Boc-dipeptide D1, wherein the substituent $R^2$ is (2,2-dimethylpropyl) carbonylamino- and the substituent $R^{24}$ is defined as dimethylamino-, as described above.

The saponified material was purified by preparative HPLC (4 mg, 21%). HPLC (purity)=97.6%; MS (electrospray), (M−H)−; 836.4 and (M+H)+; 838.4. $^1$H NMR (400 MHz, DMSO-$d_6$) δ 12.5–12.3 (m, 1H), 9.90 (s, 1H), 8.53 (s, 1H), 8.07 (d, J=8.4 Hz, 1H), 7.63–7.45 (m, 1H), 7.45–7.30 (m, 2H), 7.18–7.10 (m, 3H), 6.98 (dd, J=7.2, 7.2 Hz, 1H), 6.9–6.75 (m, 1H), 5.8–5.63 (m, 2H), 5.17 (d, J=17.2 Hz, 1H), 3.10 (s, (d, J=11.5 Hz, 1H), 4.68–4.53 (m, 1H), 4.32–4.27 (m, 1H), 4.1–3.9 (m, 1H), 3.10 (s, 6H), 2.95–2.88 (m, 1H), 2.88–2.77 (m, 1H), 2.42 (s, 2H), 2.35–2.23 (m, 2H), 2.02 (dd, J=8.5, 8.5 Hz, 1H), 1.56–1.48 (m, 1H), 1.33–1.22 (m, 1H), 1.2–1.13 (m, 1H), 1.03 (s, 9H), 1.01 (s, 9H), 0.99–0.92 (m, 2H).

Example 9
NS3—NS4A Protease Assay

The enzymatic assay used to evaluate the present compound is described in WO 00/09543 and WO 00/59929.

Example 10
Cell Based HCV RNA Replication Assay

Cell Culture

Huh7 cells that stably maintain a subgenomic HCV replicon were established as previously described (Lohman et al., 1999. Science 285: 110–113) and designated as the S22.3 cell-line. S22.3 cells are maintained in Dulbecco's Modified Earle Medium (DMEM) supplemented with 10% FBS and 1 mg/mL neomycin (Standard Medium). During the assay, DMEM medium supplemented with 10% FBS, containing 0.5% DMSO and lacking neomycin was used (Assay Medium). 16 hours prior to compound addition, S22.3 cells are trypsinized and diluted to 50 000 cells/ml in Standard Medium. 200 μL (10 000 cells) are distributed into each well of a 96-well plate. The plate was then incubated at 370 with 5% $CO_2$ until the next day.

Reagents and Materials:

| Product | Company | Catalog # | Storage |
|---|---|---|---|
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Neomycin (G418) | Gibco-BRL | 10131-027 | −20° C./4° C. |
| Trypsin-EDTA | Gibco-BRL | 25300-054 | −20° C./4° C. |
| 96-well plates | Costar | 3997 | RT |
| PVDF 0.22 μm Filter Unit | Millipore | SLGV025LS | RT |
| Deep-Well Titer Plate Polypropylene | Beckman | 267007 | RT |

Preparation of Test Compound

10 μL of test compound (in 100% DMSO) was added to 2 ml of Assay Medium for a final DMSO concentration of 0.5% and the solution was sonicated for 15 min and filtered through a 0.22 μM Millipore Filter Unit. 900 μl was transferred into row A of a Polypropylene Deep-Well Titer Plate. Rows B to H, contain 400 μL aliquots of Assay Medium (containing 0.5% DMSO), and are used to prepare serial dilutions (½) by transferring 400 μl from row to row (no compound was included in row H).

Application of Test Compound to Cells

Cell culture medium was aspirated from the 96-well plate containing the S22.3 cells. 175 μL of assay medium with the appropriate dilution of test compound was transferred from each well of the compound plate to the corresponding well of the cell culture plate (row H was used as the "No inhibition control"). The cell culture plate was incubated at 370 with 5% $CO_2$ for 72 h.

Extraction of Total Cellular RNA

Following the 72 h incubation period, the total cellular RNA was extracted from the S22.3 cells of the 96-well plate using the RNeasy 96 kit (Qiagen®, RNeasy Handbook. 1999.). Briefly, assay medium was completely removed from cells and 100 μL of RLT buffer (Qiagen®) containing 143 mM β-mercaptoethanol was added to each well of the 96-well cell-culture plate. The microplate was gently shaken for 20 sec. 100 μL of 70% ethanol was then added to each microplate well, and mixed by pipelting. The lysate was removed and applied to the wells of a RNeasy 96 (Qiagen®) plate that was placed on top of a Qiagen® Square-Well Block. The RNeasy 96 plate was sealed with tape and the Square-Well Block with the RNeasy 96 plate was loaded into the holder and placed in a rotor bucket of a 4K15C centrifuge. The sample was centrifuged at 6000 rpm (~5600×g) for 4 min at room temperature. The tape was removed from the plate and 0.8 mL of Buffer RW1 (Qiagen® RNeasy 96 kit) was added to each well of the RNeasy 96 plate. The RNeasy 96 plate was sealed with a new piece of tape and centrifuged at 6000 rpm for 4 min at room temperature. The RNeasy 96 plate was placed on top of another clean Square-Well Block, the tape removed and 0.8 mL of Buffer RPE (Qiagen®) RNeasy 96 kit) was added to each well of the RNeasy 96 plate. The RNeasy 96 plate was sealed with a new piece of tape and centrifuged at 6000 rpm for 4 min at room temperature. The tape was removed and another 0.8 mL of Buffer RPE (Qiagen® RNeasy 96 kit) was added to each well of the RNeasy 96 plate. The RNeasy 96 plate was sealed with a new piece of tape and centrifuged at 6000 rpm for 10 min at room temperature. Tape was removed, the RNeasy 96 plate was placed on top of a rack containing 1.2-mL collection microtubes. The RNA was eluted by adding 50 μL of RNase-free water to each well, sealing plate with a new piece of tape and incubated for 1 min at room temperature. The plate was then centrifuged at 6000 rpm for 4 min at room temperature. The elution step was repeated with a second volume of 50 μL RNase-free water. The microtubes with total cellular RNA are stored at −70°.

Quantification of Total Cellular RNA

RNA was quantified on the STORM® system (Molecular Dynamics®) using the RiboGreen® RNA Quantification Kit (Molecular Probes®)). Briefly, the RiboGreen reagent was diluted 200-fold in TE (10 mM Tris-HCl pH=7.5, 1 mM EDTA). Generally, 50 μL of reagent was diluted in 10 mL TE. A Standard Curve of ribosomal RNA was diluted in TE to 2 μg/mL and pre-determined amounts (100, 50, 40, 20, 10, 5, 2 and 0 μL) of the ribosomal RNA solution are then transferred in a new 96-well plate (COSTAR # 3997) and the volume was completed to 100 μL with TE. Generally, column 1 of the 96-well plate was used for the standard curve and the other wells are used for the RNA samples to be quantified. 10 μL of each RNA sample that was to be quantified, was transferred to the corresponding well of the 96-well plate and 90 μL of TE was added. One volume (100

μL) of diluted RiboGreen reagent was added to each well of the 96-well plate and incubated for 2 to 5 minutes at room temperature, protected from light (a 10/L RNA sample in a 200 μL final volume generates a 20× dilution). The fluorescence intensity of each well was measured on the STORM® system (Molecular Dynamics®). A standard curve was created on the basis of the known quantities of the ribosomal RNA and the resulting fluorescent intensities. The RNA concentration in the experimental samples was determined from the standard curve and corrected for the 20× dilution.

Reagents and Materials:

| Product | Company | Catalog # | Storage |
|---|---|---|---|
| DEPC | Sigma | D5758 | 4° C. |
| EDTA | Sigma | E5134 | RT |
| Trizma-Base | Sigma | T8524 | RT |
| Trizma-HCl | Sigma | T7149 | RT |
| Collection Tube Strips | Qiagen | 19562 | RT |
| Ribogreen RNA Quantitation Kit | Molecular Probe | R11490 | −20° C. |
| Rneasy 96 Kit | Qiagen | 74183 | RT |
| Square-Well Blocks | Qiagen | 19573 | RT |

Real-Time RT-PCR

The Real-Time RT-PCR was performed on the ABI Prism 7700 Sequence Detection System using the TaqMan EZ RT-PCR Kit from (Perkin-Elmer Applied Biosystems®). RT-PCR was optimized for the quantification of the 5' IRES of HCV RNA by using the Taqman technology (Roche Molecular Diagnostics Systems) similar to the technique previously described (Martell et al., 1999. J. Clin. Microbiol. 37: 327–332). The system exploits the 5'-3' nucleolytic activity of AmpliTaq DNA polymerase. Briefly, the method utilizes a dual-labeled fluorogenic hybridization probe (PUTR Probe) that specifically anneals to the template between the PCR primers (primers 8125 and 7028). The 5' end of the probe contains a fluorescent reporter (6-carboxyfluorescein [FAM]) and the 3' end contains a fluorescent quencher (6-carboxytetramethylrhodamine [TAMRA]). The FAM reporter's emission spectrum was suppressed by the quencher on the intact hybridization probe. Nuclease degradation of the hybridization probe releases the reporter, resulting in an increase in fluorescence emission. The ABI Prism 7700 sequence detector measures the increase in fluorescence emission continuously during the PCR amplification such that the amplified product was directly proportion to the signal. The amplification plot was analysed early in the reaction at a point that represents the logarithmic phase of product accumulation. A point representing a defined detection threshold of the increase in the fluorescent signal associated with the exponential growth of the PCR product for the sequence detector was defined as the cycle threshold ($C_T$). $C_T$ values are inversely proportional to the quantity of input HCV RNA; such that under identical PCR conditions, the larger the starting concentration of HCV RNA, the lower the $C_T$. A standard curve was created automatically by the ABI Prism 7700 detection system by plotting the $C_T$ against each standard dilution of known HCV RNA concentration.

Reference samples for the standard curve are included on each RT-PCR plate. HCV Replicon RNA was synthesized (by T7 transcription) in vitro, purified and quantified by $OD_{260}$. Considering that 1 μg of this RNA=$2.15 \times 10^{11}$ RNA copies, dilutions are made in order to have $10^8$, $10^7$, $10^5$, $10^4$, $10^3$ or $10^2$ genomic RNA copies/5 μL. Total cellular Huh-7 RNA was also incorporated with each dilution (50 ng/5 μL). 5 μL of each reference standard (HCV Replicon+Huh-7 RNA) was combined with 45 μL of Reagent Mix, and used in the Real-Time RT-PCR reaction.

The Real-Time RT-PCR reaction was set-up for the experimental samples that were purified on RNeasy 96—well plates by combining 5 μL of each total cellular RNA sample with 45 μL of Reagent Mix.

Reagents and Materials:

| Product | COMPANY | Catalog # | Storage |
|---|---|---|---|
| TaqMan EZ RT-PCR Kit | PE Applied Biosystems | N808-0236 | −20° C. |
| MicroAmp Optical Caps | PE Applied Biosystems | N801-0935 | RT |
| MicroAmp Optical 96-Well Reaction Plate | PE Applied Biosystems | N801-0560 | RT |

Reagent Mix Preparation:

| Component | Volume for one sample (μL) | Volume for One Plate (μL) (91 samples + Dead Volume) | Final conc. |
|---|---|---|---|
| Rnase-free water | 16.5 | 1617 | |
| 5X TaqMan EZ buffer | 10 | 980 | 1X |
| $Mn(OAc)_2$ (25 mM) | 6 | 588 | 3 mM |
| dATP (10 mM) | 1.5 | 147 | 300 μM |
| dCTP (10 mM) | 1.5 | 147 | 300 μM |
| dGTP (10 mM) | 1.5 | 147 | 300 μM |
| dUTP (20 mM) | 1.5 | 147 | 600 μM |
| Forward Primer (10 μM) | 1 | 98 | 200 nM |
| Reverse Primer (10 μM) | 1 | 98 | 200 nM |
| PUTR probe (5 μM) | 2 | 196 | 200 nM |
| rTth DNA polymerase (2.5 U/μL) | 2 | 196 | 0.1 U/μL |
| AmpErase UNG (1 U/μL) | 0.5 | 49 | 0.01 U/μL |
| Total Volume | 45 | 4410 | |

```
Forward Primer Sequence:
5'-ACG CAG AAA GCG TCT AGC CAT    (SEQ ID. 1)
GGC GTT AGT-3'

Reverse Primer Sequence:
5'-TCC CGG GGC ACT CGC AAG        (SEQ ID NO. 2)
CAC CCT ATC AGG-3'
```

Note: Those primers amplify a region of 256-nt present within the 5' untranslated region of HCV.

| PUTR Probe Sequence (SEQ ID NO. 3): |6FAM|- TGG TCT GCG GAA CCG GTG AGT ACA CC -|TAMRA| |
|---|

No Template Controls (NTC): On each plate, 4 wells are used as "NTC". For these controls, 5 µl of water are added to the well in place of RNA.

Thermal Cycling Conditions:

| | | |
|---|---|---|
| 50° C. | 2 min | |
| 60° C. | 30 min | |
| 95° C. | 5 min | |
| 95° C. | 15 sec | } for 2 cycles |
| 60° C. | 1 min | |
| 90° C. | 15 sec | } for 40 cycles |
| 60° C. | 1 min | |

Following the termination of the RT-PCR reaction the data analysis requires setting of threshold fluorescence signal for the PCR plate and a standard curve was constructed by plotting the $C_T$ value versus RNA copy number used in each reference reaction. The $C_T$ values obtained for the assay samples are used to interpolate an RNA copy number based on the standard curve. Finally, the RNA copy number was normalized (based on the RiboGreen RNA quantification of the total RNA extracted from the cell culture well) and expressed as genome equivalents/µg of total RNA [g.e./µg].

The RNA copy number [g.e./µg] from each well of the cell culture plate was a measure of the amount of replicating HCV RNA in the presence of various concentrations of inhibitor. The % inhibition was calculated with the following equation:

$$100-[(g.e./\mu g\ inh)/(g.e./\mu g\ ctl) \times 100].$$

A non-linear curve fit with the Hill model was applied to the inhibition-concentration data, and the 50% effective concentration ($EC_{50}$) was calculated by the use of SAS software (Statistical Software System; SAS Institute, Inc. Cary, N.C.).

When the compounds of this invention were evaluated in the preceding enzymatic and cell based assays, the compounds were found to be highly active. More specifically, the compounds had $IC_{50}$ values below 0.1 µM in the NS3-NS4A protease assay, and $EC_{50}$ values of 0.5 µM and below in the cell based HCV RNA replication assay.

Example 11

Specificity Assays

The specificity assays which are used to evaluate the selectivity of compounds according to this invention are described in WO 00/09543.

When the compounds are evaluated in the specificity assays, the compounds of formula 1 are found to be selective in that they do not show significant inhibition in the Human Leukocyte Elastase and Cathepsin B assays.

Table of Compounds

The following table lists compounds representative of the invention. All compounds listed in the Table were found to be active in the assays as described in Examples 9 and 10.

TABLE 1

| Cpd. | B | R³ | R² | R²⁴ | m/z (M + H)⁺ |
|---|---|---|---|---|---|
| 11 | *t-Bu* | *t-Bu* | *NHAc* | —OCH₃ | 749.3 |

TABLE 1-continued

| # | R1 | R2 | R3 | R4 | Mass |
|---|---|---|---|---|---|
| 12 | cyclopentyl | t-butyl | -NH-C(O)-CH3 | —OCH₃ | 761.3 |
| 13 | cyclohexyl | t-butyl | -NH-C(O)-CH3 | —OCH₃ | 775.4 |
| 14 | phenyl | t-butyl | -NH-C(O)-CH3 | —OCH₃ | 769.4 |
| 15 | t-pentyl | t-butyl | -NH-C(O)-CH3 | —OCH₃ | 763.4 |
| 16 | cyclopentyl | cyclohexyl | -NH-C(O)-CH3 | —OCH₃ | 787.3 |
| 17 | cyclopentyl | t-butyl | -NH-cyclopentyl | —OCH₃ | 787.4 |
| 18 | phenyl | t-butyl | -NH-C(O)-CH2-C(CH3)3 | —N(CH₃)₂ | 838.3 |

What is claimed is:

1. A racemate, diastereoisomer, or optical isomer of a compound of formula (I):

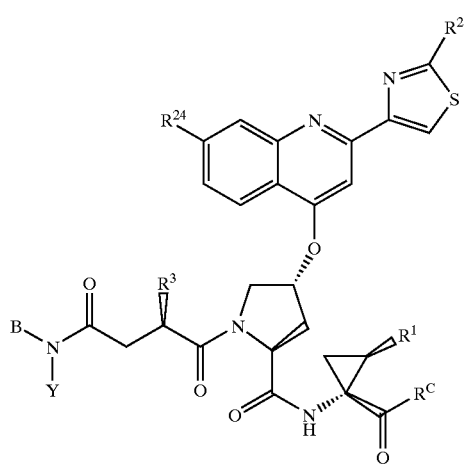

wherein:

B is $(C_{2-10})$alkyl, $(C_{3-7})$cycloalkyl or $(C_{1-4})$alkyl-$(C_{3-7})$cycloalkyl,
 a) wherein said cycloalkyl and alkyl-cycloalkyl may be mono-, di- or tri-substituted with $(C_{1-3})$alkyl; and
 b) wherein said alkyl, cycloalkyl and alkyl-cycloalkyl may be mono- or di-substituted with substituents selected from hydroxy and O—$(C_{1-4})$alkyl; and
 c) wherein each of said alkyl groups may be mono-, di- or tri-substituted with halogen; and
 d) wherein in each of said cycloalkyl groups being 5-, 6- or 7-membered, one or two —CH$_2$-groups not being directly linked to each other may be replaced by —O— such that the O-atom is linked to the N atom to which B is attached via at least two C-atoms; or B is phenyl, $(C_{1-3})$alkyl-phenyl, heteroaryl or $(C_{1-3})$alkyl-heteroaryl, wherein the heteroaryl-groups are 5- or 6-membered having from 1 to 3 heteroatoms selected from N, O and S; wherein said phenyl and heteroaryl groups may be mono-, di- or trisubstituted with substituents selected from halogen, —OH, $(C_{1-4})$alkyl, O—$(C_{1-4})$alkyl, S—$(C_{1-4})$alkyl, —NH$_2$, —NH(($C_{1-4}$)alkyl) and —N(($C_{1-4}$)alkyl)$_2$, —CONH$_2$ and —CONH—$(C_{1-4})$alkyl;

Y is H or $(C_{1-6})$alkyl;

$R^3$ is $(C_{1-6})$alkyl, $(C_{3-7})$cycloalkyl or $(C_{1-3})$alkyl-$(C_{3-7})$cycloalkyl, wherein each of said cycloalkyl groups may be mono-, di- or tri-substituted with substituents selected from halogen, —OH, $(C_{1-4})$alkyl, O—$(C_{1-4})$alkyl, S—$(C_{1-4})$alkyl, —NH$_2$, —NH(($C_{1-4}$)alkyl), —N(($C_{1-4}$)alkyl)$_2$, —COOH and —CONH$_2$;

$R^2$ is $R^{20}$, —NR$^{21}$R$^{22}$, —NR$^{22}$COR$^{20}$, —NR$^{22}$COOR$^{20}$ or —NR$^{22}$CONR$^{23}$R$^{21}$, wherein
 $R^{20}$ is selected from $(C_{1-8})$alkyl, $(C_{3-7})$cycloalkyl and $(C_{1-4})$alkyl-$(C_{3-7})$cycloalkyl, wherein said alkyl, cycloalkyl and alkyl-cycloalkyl may be mono-, di- or tri-substituted with $(C_{1-3})$alkyl; and
 $R^{21}$ is H or $R^{20}$,
 $R^{22}$ and $R^{23}$ are independently selected from H and methyl, and
 $R^{24}$ is selected from —O—$(C_{1-4})$alkyl, —NH(($C_{1-4}$)alkyl) and —N(($C_{1-4}$)alkyl)$_2$;

$R^1$ is $(C_{1-6})$alkyl or $(C_{2-6})$alkenyl; and $R^C$ is hydroxy or NHSO$_2$R$^S$ wherein $R^S$ is $(C_{1-6})$alkyl, $(C_{3-7})$cycloalkyl, $(C_{1-6})$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; all of which optionally being mono-, di- or tri-substituted with substituents selected from halogen, hydroxy, cyano, $(C_{1-4})$alkyl, O—$(C_{1-6})$alkyl, —CO—NH$_2$, —CO—NH(($C_{1-4}$)alkyl), —CO—N(($C_{1-4}$)alkyl)$_2$, —NH$_2$, —NH(($C_{1-4}$)alkyl) and —N(($C_{1-4}$)alkyl)$_2$, wherein $(C_{1-4})$alkyl and O—$(C_{1-6})$alkyl are optionally mono-, di- or trisubstituted with halogen; and all of which optionally being monosubstituted with nitro;

or a pharmaceutically acceptable salt or ester thereof.

2. The compound according to claim 1, wherein

B is $(C_{2-10})$alkyl, $(C_{3-7})$cycloalkyl or $(C_{1-4})$alkyl-$(C_{3-7})$cycloalkyl,
 a) wherein said cycloalkyl and alkyl-cycloalkyl may be mono-, di- or tri-substituted with $(C_{1-3})$alkyl; and
 b) wherein said alkyl, cycloalkyl and alkyl-cycloalkyl may be mono- or di-substituted with substituents selected from hydroxy and O—$(C_{1-4})$alkyl; and
 c) wherein all said alkyl-groups may be mono-, di- or tri-substituted with halogen; and
 d) wherein in said cycloalkyl-group being 5-, 6- or 7-membered, one or two —CH$_2$-groups not being directly linked to each other may be replaced by —O— such that the O-atom is linked to the N atom to which B is attached via at least two C-atoms; or B is phenyl, $(C_{1-3})$alkyl-phenyl, heteroaryl or $(C_{1-3})$alkyl-heteroaryl, wherein the heteroaryl-groups are 5- or 6-membered having from 1 to 3 heteroatoms selected from N, O and S; wherein said phenyl and heteroaryl groups may be mono-, di- or trisubstituted with substituents selected from halogen, —OH, $(C_{1-4})$alkyl, O—$(C_{1-4})$alkyl, S—$(C_{1-4})$alkyl, —$NH_2$, —NH(($C_{1-4}$ alkyl) and —N(($C_{1-4}$)alkyl)$_2$, —$CONH_2$ and —CONH—$(C_{1-4})$alkyl;

Y is H or $(C_{1-6})$alkyl;

$R^3$ is $(C_{1-6})$alkyl, $(C_{3-7})$cycloalkyl or $(C_{1-3})$alkyl-$(C_{3-7})$ cycloalkyl, wherein said cycloalkyl groups may be mono-, di- or tri-substituted with substituents selected from halogen, —OH, $(C_{1-4})$alkyl, O—$(C_{1-4})$alkyl, S—$(C_{1-4})$alkyl, —$NH_2$, —NH(($C_{1-4})$alkyl) and —N(($C_{1-4})$alkyl)$_2$, —COOH and —$CONH_2$;

$R^2$ is $R^{20}$ is —$NR^{21}R^{22}$, —$NR^{22}COR^{20}$, —$NR^{22}COOR^{20}$ and —$NR^{22}CONR^{23}R^{21}$, wherein $R^{20}$ is selected from $(C_{1-8})$alkyl, $(C_{3-7})$ cycloalkyl and $(C_{1-4})$alkyl-$(C_{3-7})$cycloalkyl, wherein said cycloalkyl and alkyl-cycloalkyl may be mono-, di- or tri-substituted with $(C_{1-3})$alkyl; and $R^{21}$ is H or $R^{20}$, $R^{22}$ and $R^{23}$ are independently selected from H and methyl, and $R^{24}$ is selected from: —O—$(C_{1-4})$alkyl, NH(($C_{1-4})$alkyl) and —N(($C_{1-4})$alkyl)$_2$;

$R^1$ is $(C_{1-6})$alkyl or $(C_{2-6})$alkenyl; and $R^C$ is hydroxy or $NHSO_2R^S$ wherein $R^S$ is $(C_{1-6})$alkyl, $(C_{3-7})$cycloalkyl or $(C_1)$alkyl-$(C_{3-7})$cycloalkyl, phenyl, naphthyl, pyridinyl, $(C_{1-4})$alkyl-phenyl, $(C_{1-4})$alkyl-naphthyl or $(C_{1-4})$alkyl-pyridinyl; all of which being optionally mono-, di- or tri-substituted with substituents selected from halogen, hydroxy, cyano, $(C_{1-4})$ alkyl, O—$(C_{1-6})$alkyl, —CO—$NH_2$, —CO—NH(($C_{1-4})$ alkyl), —CO—N(($C_{1-4})$alkyl)$_2$, —$NH_2$, —NH(($C_1)$alkyl) and —N(($C_{1-4})$alkyl)$_2$; and all of which optionally being monosubstituted with nitro;

or a pharmaceutically acceptable salt or ester thereof.

3. The compound according to claim 1, wherein B is $(C_{2-10})$alkyl, $(C_{3-7})$cycloalkyl, $(C_{1-3})$alkyl-$(C_{3-7})$cycloalkyl or phenyl, a) wherein said cycloalkyl, alkyl-cycloalkyl and phenyl may be mono-, di- or tri-substituted with $(C_{1-3})$alkyl; and b) wherein said alkyl, cycloalkyl, alkyl-cycloalkyl and phenyl may be mono- or di-substituted with substituents selected from hydroxy and O—$(C_{1-4})$alkyl; and c) wherein each of said alkyl-groups and phenyl may be mono-, di- or tri-substituted with fluorine or mono-substituted by chlorine or bromine, and d) wherein in each of said cycloalkyl-groups being 5-, 6- or 7-membered, one or two —$CH_2$-groups not being directly linked to each other may be replaced by —O— such that the O-atom is linked to the N atom to which B is attached via at least two C-atoms.

4. The compound according to claim 3, wherein B is selected from ethyl, n-propyl, i-propyl, n-butyl, 1-methylpropyl, 2-methylpropyl, tert-butyl, cyclopropyl, cyclobutyl, cyclopentyl, cyclohexyl, cyclopropylmethyl, cyclobutylmethyl, cyclopentylmethyl, cyclohexylmethyl and phenyl;

a) wherein each of said groups optionally being mono-, di- or tri-substituted with substituents selected from methyl and ethyl;

b) wherein each of said groups optionally being mono- or di-substituted with substituents selected from hydroxy, methoxy and ethoxy; and c) wherein each of said alkyl groups and phenyl may be mono-, di- or tri-substituted with fluorine or mono-substituted by chlorine or bromine; and d) wherein in each of said cycloalkyl-groups being 5-, 6- or 7-membered, one or two —$CH_2$-groups not being directly linked to each other may be replaced by —O— such that the O-atom is linked to the N atom to which B is attached via at least two C-atoms.

5. The compound according to claim 3 wherein B is $(C_{3-8})$alkyl, $(C_{5-6})$cycloalkyl, or phenyl, wherein each of said groups may be mono- or di-substituted with methyl.

6. The compound according to claim 3 wherein B is selected from 1,1-dimethylethyl, 1,1-dimethylpropyl, cyclopropyl, cyclobutyl, cyclopentyl, cyclohexyl, 1-methylcyclopentyl, 1-methylcyclohexyl and phenyl.

7. The compound according to claim 1 wherein Y is H.

8. The compound according to claim 1, wherein $R^3$ is $(C_{1-3})$alkyl, $(C_{3-7})$cycloalkyl or $(C_{1-6})$alkyl-$(C_{3-7})$ cycloalkyl, wherein each of said cycloalkyl groups are optionally substituted by 1 to 3 substituents selected from $(C_{1-4})$alkyl.

9. The compound according to claim 8, wherein $R^3$ is selected from 1-methylethyl, 1,1-dimethylethyl, 1-methylpropyl, 2-methylpropyl, 1,1-dimethylpropyl, 1,2-dimethylpropyl, 2,2-dimethylpropyl, cyclopentyl, cyclohexyl, 1-methylcyclopentyl, 1-methylcyclohexyl, cyclopentylmethyl, cyclohexylmethyl, (1-methylcyclopentyl)methyl and (1-methylcyclohexyl)methyl.

10. The compound according to claim 9, wherein $R^3$ is selected from 1,1-dimethylethyl, cyclopentyl, cyclohexyl and 1-methylcyclohexyl.

11. The compound according to claim 1, wherein $R^2$ is $R^{20}$, —$NR^{21}R^{22}$, —$NR^{22}COR^{20}$, —$NR^{22}COOR^{20}$ or —$NR^{22}CONR^{23}R^{21}$, wherein $R^{20}$ is selected from $(C_{1-4})$alkyl, $(C_{3-7})$cycloalkyl and $(C_{1-3})$alkyl-$(C_{3-7})$cycloalkyl, wherein said alkyl, cycloalkyl and alkyl-cycloalkyl may be mono-, di- or tri-substituted with $(C_{1-3})$alkyl; and $R^{21}$ is H or $R^{20}$; and $R^{22}$ and $R^{23}$ are independently selected from H and methyl.

12. The compound according to claim 11, wherein $R^2$ is —$NHR^{21}$ or —$NHCOR^{20}$, wherein $R^{20}$ and $R^{21}$ are defined as in claim 11.

13. The compound according to claim 12, wherein $R^{20}$ and $R^{21}$ are independently selected from: methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl and cyclohexylmethyl, each of which optionally being mono- or di-substituted with methyl or ethyl.

14. The compound according to claim 1, wherein $R^{24}$ is selected from $OCH_3$ and $N(CH_3)_2$.

15. The compound according to claim 1, wherein $R^1$ is ethyl or vinyl.

16. The compound according to claim 1, wherein $R^C$ is selected from hydroxy or $NHSO_2R^S$ wherein $R^S$ is methyl, ethyl, n-propyl, i-propyl, n-butyl, 1-methylpropyl, 2-methylpropyl, tert-butyl, cyclopropyl, cyclobutyl, cyclopentyl, cyclohexyl, cyclopropylmethyl, cyclobutylmethyl, cyclopentylmethyl, cyclohexylmethyl, phenyl, naphthyl, pyridinyl, phenylmethyl, naphthylmethyl or pyridinylmethyl, each of which optionally being substituted with one or more substituents selected from a) one, two or three substituents selected from fluorine and methyl;
b) one or two substituents selected from hydroxy, trifluoromethyl, methoxy and trifluoromethoxy; and
c) one substituent selected from chlorine, bromine, cyano, nitro, —CO—NH$_2$, —CO—NHCH$_3$, —CO—N(CH$_3$)$_2$, —NH$_2$, —NH(CH$_3$) and —N(CH$_3$)$_2$.

17. The compound according to claim 16, wherein $R^C$ is selected from hydroxy, NHSO$_2$-methyl, NHSO$_2$-ethyl, NHSO$_2$-(1-methyl)ethyl, NHSO$_2$-propyl, NHSO$_2$-cyclopropyl, NHSO$_2$-cyclopropylmethyl, NHSO$_2$-cyclobutyl, NHSO$_2$-cyclopentyl and NHSO$_2$-phenyl.

18. The compound according to claim 17, wherein $R^C$ is hydroxy.

19. The compound according to claim 17, wherein $R^C$ is NHSO$_2$-cyclopropyl.

20. The compound according to claim 1, wherein:
B is (C$_{3-8}$)alkyl, (C$_{5-6}$)cycloalkyl, or phenyl, each of said groups being optionally mono- or di-substituted with methyl;
Y is H or methyl;
$R^3$ is (C$_{1-6}$)alkyl or (C$_{3-7}$)cycloalkyl, said cycloalkyl being optionally substituted by 1 to 3 substituents selected from (C$_{1-4}$)alkyl;
$R^2$ is $R^{20}$, —NR$^{21}$R$^{22}$, —NR$^{22}$COR$^{20}$, —NR$^{22}$COOR$^{20}$ and —NR$^{22}$CONR$^{23}$R$^{21}$,
wherein $R^{20}$ is selected from methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, cyclopropylmethyl, cyclobutylmethyl, cyclopentylmethyl and cyclohexylmethyl; all of which optionally being substituted by 1 to 3 substituents selected from methyl and ethyl;
$R^{21}$ is H or $R^{20}$;
$R^{22}$ and $R^{23}$ are independently selected from H and methyl;
$R^{24}$ is —OCH$_3$ or —N(CH$_3$)$_2$;
$R^1$ is ethyl or vinyl; and
$R^C$ is hydroxy, NHSO$_2$-methyl, NHSO$_2$-ethyl, NHSO$_2$-(1-methyl)ethyl, NHSO$_2$-propyl, NHSO$_2$-cyclopropyl, NHSO$_2$-cyclopropylmethyl, NHSO$_2$-cyclobutyl, NHSO$_2$-cyclopentyl or NHSO$_2$-phenyl.

21. The compound according to claim 1, wherein B is selected from 1,1-dimethylethyl, 1,1-dimethylpropyl, cyclopropyl, cyclobutyl, cyclopentyl, cyclohexyl, 1-methylcyclopentyl, 1-methylcyclohexyl and phenyl; Y is H; $R^3$ is selected from 1,1-dimethylethyl, cyclopentyl, cyclohexyl and 1-methylcyclohexyl; $R^2$ is —NHR$^{21}$ or —NHCOR$^{20}$, wherein $R^{20}$ and $R^{21}$ are independently selected from: methyl, ethyl, n-propyl, i-propyl, n-butyl, 1-methylpropyl, 2-methylpropyl, tert-butyl, 2,2-dimethylpropyl, 1,1-dimethylpropyl, 1,2-dimethylpropyl, 1,2,2-trimethylpropyl, cyclopropyl, cyclobutyl, cyclopentyl, cyclohexyl, all of which optionally being mono- or di-substituted with methyl or ethyl; $R^{24}$ is —OCH$_3$; $R^1$ is vinyl and $R^C$ is hydroxy or NHSO$_2$-cyclopropyl.

22. The compound according to claim 21, wherein B is selected from 1,1-dimethylethyl, 1,1-dimethylpropyl, cyclopentyl, cyclohexyl and phenyl; $R^3$ is selected from 1,1-dimethylethyl and cyclohexyl, $R^C$ is hydroxy and Y, $R^2$, $R^{24}$ and $R^1$ are defined as in claim 21.

23. The compound according to claim 1, of the formula

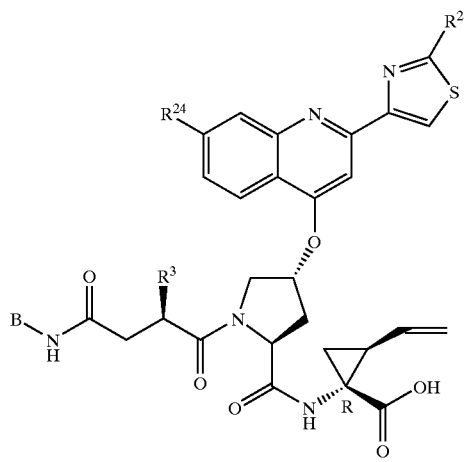

wherein B, $R^3$, $R^2$, and $R^{24}$ are defined according to the following table

| Cpd. | B | $R^3$ | $R^2$ | $R^{24}$ |
|---|---|---|---|---|
| 11 | t-Bu | t-Bu | NHC(O)CH$_3$ | —OCH$_3$ |
| 12 | cyclopentyl | t-Bu | NHC(O)CH$_3$ | —OCH$_3$ |
| 13 | cyclohexyl | t-Bu | NHC(O)CH$_3$ | —OCH$_3$ |
| 14 | phenyl | t-Bu | NHC(O)CH$_3$ | —OCH$_3$ |
| 15 | 1,1-dimethylpropyl | t-Bu | NHC(O)CH$_3$ | —OCH$_3$ |
| 16 | cyclopentyl | cyclohexyl | NHC(O)CH$_3$ | —OCH$_3$ |

-continued

| Cpd. | B | R³ | R² | R²⁴ |
|---|---|---|---|---|
| 17 |  |  |  | —OCH₃ |
| 18 |  |  | 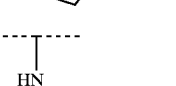 | —N(CH₃)₂ |

24. A pharmaceutical composition comprising an anti-hepatitis C virally effective amount of a compound of formula I according to claim 1 or a pharmaceutically acceptable salt or ester thereof, in admixture with at least one pharmaceutically acceptable carrier medium or auxiliary agent.

25. The pharmaceutical composition according to claim 24 further comprising a therapeutically effective amount of at least one other antiviral agent.

26. The pharmaceutical composition according to claim 25, wherein said antiviral agent is ribavirin.

27. The pharmaceutical composition according to claim 25, wherein said antiviral agent is selected from another anti-HCV agent, HIV inhibitor, HAV inhibitor and HBV inhibitor.

28. The pharmaceutical composition according to claim 27, wherein said other anti-HCV agent is selected from immunomodulatory agents, other inhibitors of HCV NS3 protease, inhibitors of HCV polymerase and inhibitors of another target in the HCV life cycle.

29. The pharmaceutical composition according to claim 28, wherein said immunomodulatory agent is selected from α-interferon and pegylated α-interferon.

30. The pharmaceutical composition according to claim 28, wherein said inhibitor of another target in the HCV life cycle is selected from inhibitors of: helicase, NS2/3 protease and internal ribosome entry site (IRES).

31. A method for the treatment or prevention of a hepatitis C viral infection in a mammal by administering to the mammal an anti-hepatitis C virally effective amount of a compound of formula I according to claim 1, or a pharmaceutically acceptable salt or ester thereof.

32. A method for the treatment or prevention of a hepatitis C viral infection in a mammal by administering thereto an anti-hepatitis C virally effective amount of a compound of formula I according to claim 1, or a pharmaceutically acceptable salt or ester thereof in combination with at least one other antiviral agent.

33. The method according to claim 32, wherein said antiviral agent is ribavirin.

34. The method according to claim 32, wherein said other antiviral agent is selected from another anti-HCV agent, HIV inhibitor, HAV inhibitor and HBV inhibitor.

35. The method according to claim 34, wherein said other anti-HCV agent is selected from immunomodulatory agents, other inhibitors of HCV NS3 protease, inhibitors of HCV polymerase and inhibitors of another target in the HCV life cycle.

36. The method according to claim 35, wherein said immunomodulatory agent is selected from α-interferon and pegylated α-interferon.

37. The method according to claim 35, wherein said inhibitor of another target in the HCV life cycle is selected from inhibitors of: helicase, NS2/3 protease and internal ribosome entry site (IRES).

38. A method of inhibiting the replication of hepatitis C virus by exposing the virus to a hepatitis C viral NS3 protease inhibiting amount of the compound of formula (I) according to claim 1, or a pharmaceutically acceptable salt or ester thereof.

39. A process for the preparation of a compound of formula (I) according to claim 1 comprising the step of coupling a peptide of the formula (III):

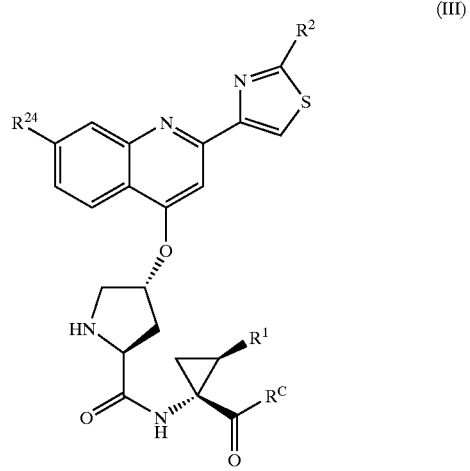

(III)

wherein $R^C$ is —O—CGP or —NHSO₂$R^S$; and $R^{24}$, $R^2$, $R^1$, and $R^S$ are defined as in claim 1 and CPG is a carboxyl protecting group;

with a succinic acid moiety of formula (II):

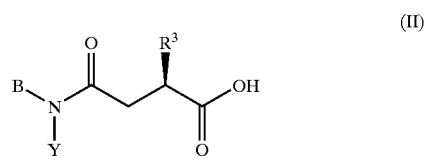

(II)

wherein B, Y and $R^3$ are defined as in claim 1.

40. An article of manufacture comprising packaging material contained within which is a composition effective to treat an HCV infection or to inhibit the NS3 protease of HCV and the packaging material comprises a label which indicates that the composition can be used to treat infection by the hepatitis C virus or to inhibit the NS3 protease of HCV, and wherein said composition comprises a compound of formula (I) of claim 1 or a pharmaceutically acceptable salt or ester thereof.

* * * * *